(12) United States Patent
Harmange et al.

(10) Patent No.: US 7,795,254 B2
(45) Date of Patent: Sep. 14, 2010

(54) BENZOMORPHOLINE DERIVATIVES AND METHODS OF USE

(75) Inventors: Jean-Christophe Harmange, Andover, MA (US); Matthew W. Martin, Arlington, MA (US); Yohannes Teffera, Topsfield, MA (US); Raju Subramanian, Thousand Oaks, CA (US); Ryan White, Somerville, MA (US); Roger Zanon, Minneapolis, MN (US); Jay Larrow, Wakefield, MA (US); Joseph F. Payack, Somerset, NJ (US); Mina Dilmeghani Seran, Ankara (TR)

(73) Assignee: Amgen Inc., Thousand Oaks, CA (US)

( * ) Notice: Subject to any disclaimer, the term of this patent is extended or adjusted under 35 U.S.C. 154(b) by 0 days.

(21) Appl. No.: 12/290,223

(22) Filed: Oct. 28, 2008

(65) Prior Publication Data

US 2009/0149454 A1  Jun. 11, 2009

Related U.S. Application Data

(60) Provisional application No. 61/000,948, filed on Oct. 29, 2007.

(51) Int. Cl.
C07D 413/12 (2006.01)
A61K 31/538 (2006.01)
(52) U.S. Cl. .................................. 514/230.5; 544/105
(58) Field of Classification Search ................. 544/105; 514/230.5
See application file for complete search history.

(56) References Cited

U.S. PATENT DOCUMENTS

| | | | |
|---|---|---|---|
| 3,755,332 | A | 8/1973 | Wasley et al. |
| 4,916,135 | A | 4/1990 | Effland et al. |
| 5,580,870 | A | 12/1996 | Barker et al. |
| 5,866,572 | A | 2/1999 | Barker et al. |
| 5,965,563 | A | 10/1999 | Buzzetti et al. |
| 6,143,764 | A | 11/2000 | Kubo et al. |
| 6,265,398 | B1 | 7/2001 | Braun et al. |
| 6,313,129 | B1 | 11/2001 | Uckun et al. |
| 6,358,962 | B2 | 3/2002 | Uckun et al. |
| 6,399,602 | B1 | 6/2002 | Barker et al. |
| 6,469,013 | B2 | 10/2002 | Uckun et al. |
| 6,495,556 | B2 | 12/2002 | Uckun et al. |
| 6,573,289 | B1 | 6/2003 | Tasaka et al. |
| 6,706,738 | B2 | 3/2004 | Clark et al. |
| 6,849,625 | B2 | 2/2005 | Lambert et al. |
| 6,897,214 | B2 | 5/2005 | Barker et al. |
| 7,071,216 | B2 | 7/2006 | Renhowe et al. |
| 7,074,800 | B1 | 7/2006 | Stokes et al. |
| 7,084,149 | B2 | 8/2006 | Tasaka et al. |
| 7,253,286 | B2 | 8/2007 | Funahashi et al. |
| 7,265,122 | B2 | 9/2007 | Wu et al. |
| 7,268,230 | B2 | 9/2007 | Hennequin |
| 7,312,330 | B2 | 12/2007 | Kelly et al. |
| 7,320,989 | B2 | 1/2008 | Anderson et al. |
| 7,425,564 | B2 | 9/2008 | Fujiwara et al. |
| 7,435,823 | B2 | 10/2008 | Potashman et al. |
| 7,531,553 | B2 | 5/2009 | Dipietro et al. |
| 7,560,558 | B2 | 7/2009 | Shimizu et al. |
| 2003/0220357 | A1 | 11/2003 | Bankston et al. |
| 2005/0043336 | A1 | 2/2005 | Hennequin et al. |
| 2005/0054662 | A1 | 3/2005 | Hennequin et al. |
| 2006/0223815 | A1 | 10/2006 | Curwen et al. |
| 2008/0312232 | A1 | 12/2008 | Kim et al. |

FOREIGN PATENT DOCUMENTS

| | | | |
|---|---|---|---|
| WO | 9623774 | A1 | 8/1996 |
| WO | 9629301 | A1 | 9/1996 |
| WO | 9629305 | A1 | 9/1996 |
| WO | 9703069 | A1 | 1/1997 |
| WO | 9935132 | A1 | 7/1999 |

OTHER PUBLICATIONS

Vippagunta et al, "Crystalline Solids" Advanced Drug Delivery Reviews, vol. 48, pp. 3-26 (2001).*
Gavezzotti, "Are Crystal Structures Predictable?" Accounts of Chemical Research, vol. 27, pp. 309-314 (1994).*
Wolff Manfred E. "Burger's Medicinal Chemistry, 5ed, Part 1" John Wiley & Sons, 1995, pp. 975-977.*
Banker, G.S. et al, "Modern Pharmaceutics, 3ed." Marcel Dekker, New York, 1996, pp. 451 and 596.*
Asano et al., Silver halide color photographic materials, Abstract 113:181318 (1990).
Chatterjee, A.K., 4-Aminoquinolines. III. Some 4-(quinolylamino)quinolines, Science and Culture 23:195 (1957).

(Continued)

*Primary Examiner*—Kahsay T Habte
(74) *Attorney, Agent, or Firm*—Joseph W. Bulock

(57) ABSTRACT

Selected benzomorpholine compounds, including 7-((6,7-bis (methyloxy)-4-quinolinyl)oxy)-N-(5-methyl-3-isoxazolyl)-2,3-dihydro-4H-1,4-benzoxazine-4-carboxamide, are effective for prophylaxis and treatment of diseases, such as VEGF mediated diseases. The invention encompasses novel compounds, analogs, prodrugs and pharmaceutically acceptable salts thereof pharmaceutical compositions and methods for prophylaxis and treatment of diseases and other maladies or conditions involving, cancer and the like. The subject invention also relates to processes for making such compounds as well as to intermediates useful in such processes.

20 Claims, No Drawings

OTHER PUBLICATIONS

Cockerill et al., Indazolylamino quinazolines and pyridopyrimidines as inhibitors of the EGFr and C-erbB-2, Bioorganic & Medicinal Chemistry Letters, 11:1401-1405 (2001).

Kasai et al., Flexible coordination networks with fluorinated backbones, remarkable ability for induced-fit enclathration of organic molecules, Journal of American Chemical Society, 122:2140-2141 (2000).

Lempert-Sreter et al., The synthesis of di(1-isoquinolinyl) and di(4-quinazolinyl) disulfides form 1(2H)-isoquinolinethiones and 4(3H)-quinazolinethiones, respectively, with tosyl chloride and sodium ethoxide, Acta Chemica Hungarica, 112(1):83-87 (1983).

Makisumi, Yasuo, The Thio-claisen rearrangement of allyl 4-quinolyl sulfides, Tetrahedron Letters, 51:6399-6403 (1966).

Maslankiewicz, M.J., Reactions of •-and •-quinolinysulfides with a nitrating mixture, Polish Journal of Chemistry, 68 (12):2545-2552 (1994).

Matsunaga et al., C17,20-lyase inhibitors. Part 2:Design, synthesis and structure-activity relationships of (2-naphthylmethyl)-1H-imidazoles as novel C17,20-lyase inhibitors, Bioorganic & Medicinal Chemistry, 12:4313-4336 (2004).

Renfrew, Alice G., Studies in the Quinoline Series. IV. Quinolyl Mercaptans and Sulfides, J. American Chemical Society, 1433-1436 (1946).

Sinyak et al., The synthesis and biological properties of the derivatives of 4-heterylmercaptoquinazoline, Khimiko-Farmatsevticheskii Zhurnal, 20(2), 168-171 (1986). Abstract 104:199594.

Thakore, P.V. et al., Studies in the synthesis of quinoline derivatives. Part VIII. Synthesis of 4:3'-methylenebis(2,2'-dichloro-4'-methylquinoline) derivatives, Journal of the Indian Chemical Society, 54(12):1204-1206 (1977).

Wyszomirski et al., Conformations of monosubstituted and disubstituted 3,4'-, 3,3'- and 4,4'-diquinolinyl sulfides studied by NMR spectroscopy, Phosphorus, Sulfur, and Silicon, 95-96:415-416 (1994).

Zhang et al., Synthesis and SAR of potent EGFR/erbB2 dual inhibitors, Bioorganic & Medicinal Chemistry Letters, 14:111-114 (2004).

Brazhko et al., Investigations of the biological activity 4-thioquinolines. Chemical Abstract 135:189745; 2001.

Konishi et al., Preparation of thioquinoline derivatives as antibacterial agents for *Helicobacter pylori*, Chemical Abstracts 125:247631; 1996.

Monti et al., IV. Chemical Abstract 55:2681; 1961.

Moszew et al., Thermal reactions of gamma-thiols in pyridine and quinoline series. Chemical Abstract 77:164418; 1972.

Zhang et al., Synthesis and antimalarial activity of 2-dialkylaminomethyl-4-(heterocyclic amino)-5,6,7,8-tetrahydronaphthol derivatives. Chemical Abstract 103:87753; 1985.

\* cited by examiner

BENZOMORPHOLINE DERIVATIVES AND METHODS OF USE

CROSS-REFERENCE TO RELATED APPLICATIONS

This application claims priority to U.S. Provisional Application Ser. No. 61/000,948 filed Oct. 29, 2007 the entirety of which is incorporated herein by reference.

FIELD OF THE INVENTION

This invention is in the field of pharmaceutical agents and specifically relates to compounds, compositions, uses and methods for treating cancer.

BACKGROUND OF THE INVENTION

Protein kinases represent a large family of proteins which play a central role in the regulation of a wide variety of cellular processes, maintaining control over cellular function. A partial list of such kinases includes abl, Akt, bcr-abl, Blk, Brk, Btk, c-kit, c-Met, c-src, c-fms, CDK1, CDK2, CDK3, CDK4, CDK5, CDK6, CDK7, CDK8, CDK9, CDK10, cRaf1, CSF1R, CSK, EGFR, ErbB2, ErbB3, ErbB4, Erk, Fak, fes, FGFR1, FGFR2, FGFR3, FGFR4, FGFR5, Fgr, flt-1, Fps, Frk, Fyn, Hck, IGF-1R, INS-R, Jak, KDR, Lck, Lyn, MEK, p38, PDGFR, PIK, PKC, PYK2, ros, tie, tie2, TRK, Yes, and Zap70. Inhibition of such kinases has become an important therapeutic target.

Certain diseases are known to be associated with deregulated angiogenesis, for example ocular neovascularisation, such as retinopathies (including diabetic retinopathy), age-related macular degeneration, psoriasis, hemangioblastoma, hemangioma, arteriosclerosis, inflammatory disease, such as a rheumatoid or rheumatic inflammatory disease, especially arthritis (including rheumatoid arthritis), or other chronic inflammatory disorders, such as chronic asthma, arterial or post-transplantational atherosclerosis, endometriosis, and neoplastic diseases, for example so-called solid tumors and liquid tumors (such as leukemias).

At the center of the network regulating the growth and differentiation of the vascular system and its components, both during embryonic development and normal growth, and in a wide number of pathological anomalies and diseases, lies the angiogenic factor known as Vascular Endothelial Growth Factor" (VEGF; originally termed "Vascular Permeability Factor", VPF), along with its cellular receptors (see G. Breier et al., Trends in Cell Biology, 6:454-456 (1996)).

VEGF is a dimeric, disulfide-linked 46-kDa glycoprotein related to "Platelet-Derived Growth Factor" (PDGF); it is produced by normal cell lines and tumor cell lines; is an endothelial cell-specific mitogen; shows angiogenic activity in in vivo test systems (e.g. rabbit cornea); is chemotactic for endothelial cells and monocytes; and induces plasminogen activators in endothelial cells, which are involved in the proteolytic degradation of extracellular matrix during the formation of capillaries. A number of isoforms of VEGF are known, which show comparable biological activity, but differ in the type of cells that secrete them and in their heparin-binding capacity. In addition, there are other members of the VEGF family, such as "Placenta Growth Factor" (PlGF) and VEGF-C.

VEGF receptors (VEGFR) are transmembranous receptor tyrosine kinases. They are characterized by an extracellular domain with seven immunoglobulin-like domains and an intracellular tyrosine kinase domain. Various types of VEGF receptor are known, e.g. VEGFR-1 (also known as flt-1), VEGFR-2 (also known as KDR), and VEGFR-3.

A large number of human tumors, especially gliomas and carcinomas, express high levels of VEGF and its receptors. This has led to the hypothesis that the VEGF released by tumor cells stimulates the growth of blood capillaries and the proliferation of tumor endothelium in a paracrine manner and through the improved blood supply, accelerate tumor growth. Increased VEGF expression could explain the occurrence of cerebral edema in patients with glioma. Direct evidence of the role of VEGF as a tumor angiogenesis factor in vivo is shown in studies in which VEGF expression or VEGF activity was inhibited. This was achieved with anti-VEGF antibodies, with dominant-negative VEGFR-2 mutants which inhibited signal transduction, and with antisense-VEGF RNA techniques. All approaches led to a reduction in the growth of glioma cell lines or other tumor cell lines in vivo as a result of inhibited tumor angiogenesis.

Angiogenesis is regarded as an absolute prerequisite for tumors which grow beyond a diameter of about 1-2 mm; up to this limit, oxygen and nutrients may be supplied to the tumor cells by diffusion. Every tumor, regardless of its origin and its cause, is thus dependent on angiogenesis for its growth after it has reached a certain size.

Three principal mechanisms play an important part in the activity of angiogenesis inhibitors against tumors: 1) Inhibition of the growth of vessels, especially capillaries, into avascular resting tumors, with the result that there is no net tumor growth owing to the balance that is achieved between cell death and proliferation; 2) Prevention of the migration of tumor cells owing to the absence of blood flow to and from tumors; and 3) Inhibition of endothelial cell proliferation, thus avoiding the paracrine growth-stimulating effect exerted on the surrounding tissue by the endothelial cells which normally line the vessels. See R. Connell and J. Beebe, Exp. Opin. Ther. Patents, 11:77-114 (2001).

VEGF's are unique in that they are the only angiogenic growth factors known to contribute to vascular hyperpermeability and the formation of edema. Indeed, vascular hyperpermeability and edema that is associated with the expression or administration of many other growth factors appears to be mediated via VEGF production.

Inflammatory cytokines stimulate VEGF production. Hypoxia results in a marked upregulation of VEGF in numerous tissues, hence situations involving infarct, occlusion, ischemia, anemia, or circulatory impairment typically invoke VEGF/VPF-mediated responses. Vascular hyperpermeability, associated edema, altered transendothelial exchange and macromolecular extravasation, which is often accompanied by diapedesis, can result in excessive matrix deposition, aberrant stromal proliferation, fibrosis, etc. Hence, VEGF-mediated hyperpermeability can significantly contribute to disorders with these etiologic features. As such, regulators of angiogenesis have become an important therapeutic target.

Angiogenesis, the process of sprouting new blood vessels from existing vasculature and arteriogenesis, the remodeling of small vessels into larger conduit vessels are both physiologically important aspects of vascular growth in adult tissues. These processes of vascular growth are required for beneficial processes such as tissue repair, wound healing, recovery from tissue ischemia and menstrual cycling. They are also required for the development of pathological conditions such as the growth of neoplasias, diabetic retinopathy, rheumatoid arthritis, psoriasis, certain forms of macular degeneration, and certain inflammatory pathologies. The inhibition of vascular growth in these contexts has also shown beneficial effects in preclinical animal models. For example, inhibition of angiogenesis by blocking vascular endothelial growth factor or its receptor has resulted in inhibition of tumor growth and in retinopathy. Also, the development of pathological pannus tissue in rheumatoid arthritis involves angiogenesis and might be blocked by inhibitors of angiogenesis.

The ability to stimulate vascular growth has potential utility for treatment of ischemia-induced pathologies such as myocardial infarction, coronary artery disease, peripheral vascular disease, and stroke. The sprouting of new vessels and/or the expansion of small vessels in ischemic tissues prevents ischemic tissue death and induces tissue repair. Certain diseases are known to be associated with deregulated angiogenesis, for example ocular neovascularization, such as retinopathies (including diabetic retinopathy), age-related macular degeneration, psoriasis, hemangioblastoma, hemangioma, arteriosclerosis, inflammatory disease, such as a rheumatoid or rheumatic inflammatory disease, especially arthritis (including rheumatoid arthritis), or other chronic inflammatory disorders, such as chronic asthma, arterial or post-transplantational atherosclerosis, endometriosis, and neoplastic diseases, for example so-called solid tumors and liquid tumors (such as leukemias).

WO 05/070891 (the entirety of which is incorporated herein by reference) describes certain benzomorpholine derivatives that are useful as VEGF inhibitors, including the following reference compound 1:

Ref. Cmpd 1

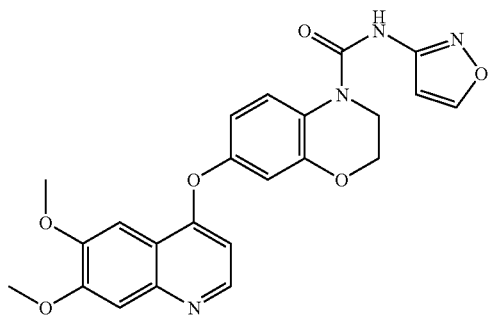

WO 05/070891 Ex. 781

The benzomorpholine compounds of the current invention possess unexpected advantages when compared to the closest compound in the prior art, reference compound 1.

DESCRIPTION OF THE INVENTION

A class of compounds useful in treating cancer and angiogenesis is defined by the following compound A Compound A

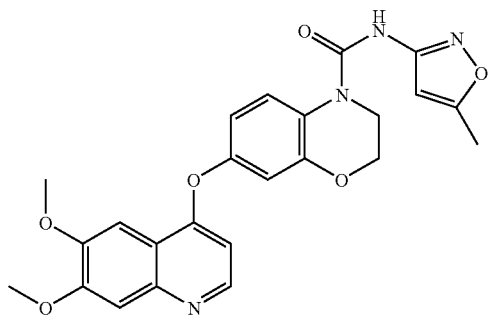

active metabolites, salts and solvates thereof.

The present invention also relates to pharmaceutical compositions containing the above-described compounds, together with a pharmaceutically acceptable vehicle or carrier.

The invention also relates to a method of treating cancer in a subject using the above compounds either alone or in combination with another therapeutic agent.

The invention also relates to a method of inhibiting angiogenesis in a subject using the above compounds either alone or in combination with another therapeutic agent.

The invention also relates to a method of treating tumors in a subject using the above compounds either alone or in combination with another therapeutic agent.

The invention also relates to a method of inhibiting tumor growth in a subject using the above compounds either alone or in combination with another therapeutic agent.

The invention also relates to a method of reducing tumor size in a subject using the above compounds either alone or in combination with another therapeutic agent.

The invention also relates to a method of inhibiting metastasis of tumors in a subject using the above compounds either alone or in combination with another therapeutic agent.

The invention also relates to a method of treating VEGF-mediated disorders in a subject using the above compounds either alone or in combination with another therapeutic agent.

The invention further relates to a process for preparing compound A, salts, and solvates thereof comprising the step of contacting a compound of the following formula I

I

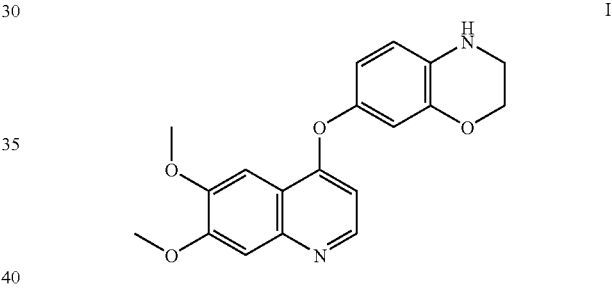

with a compound of the following formula II

II

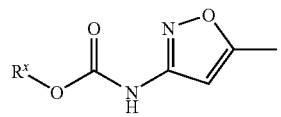

wherein $R^x$ is optionally substituted aryl or heteroaryl;

in the presence of
(1) a polar solvent; and
(2) a base

Suitable polar solvents include, but are not limited to esters, such as alkyl acetates (e.g., methyl acetate, ethyl acetate, isopropyl acetate and the like), amides (such as dimethyl formamide, N-methylpyrrolidinone, dimethyl acetamide and the like), chlorinated hydrocarbons (such as chlorinated benzene, methylene chloride, dichloro ethane and the like), ethers (such as methyl-t-butyl ether, tetrahydrofuran and the like), pyridine and n-methyl morpholine, or any combination thereof. Preferred polar solvents include ethyl acetate, isopropyl acetate and N-methylpyrrolidinone ("NMP").

Suitable bases include, but are not limited to metal hydroxides (such as lithium hydroxide, sodium hydroxide, potassium hydroxide, magnesium hydroxide and the like), organic tertiary amines (such as triethyl amine, diisopropyl amine and the like), metal alkoxides (such as potassium or sodium methoxide, ethoxide, t-butoxide and the like), metal carbonates (such as sodium or potassium carbonate and the like), bicarbonates (such as sodium or potassium bicarbonate and the like), lithium amides (such as lithium diisopropylamide and the like), lithium alkyls (such as butyl lithium and the like), pyridine and N-methyl morpholine, or any combination thereof. Preferred bases include sodium hydroxide, potassium hydroxide, sodium t-butoxide, potassium t-butoxide, sodium carbonate and potassium carbonate.

The present invention further relates to a process wherein the compound of formula II is

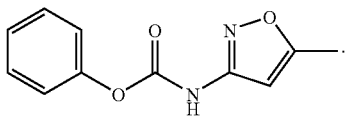

The present invention further relates to a process wherein the compound of formula II is prepared by contacting

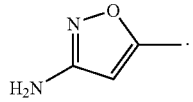

with a compound of the following formula III

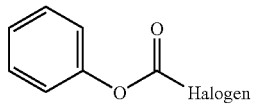

III in the presence of
(1) a polar solvent; and
(2) a base.

The present invention further relates to a process wherein the compound of formula III is

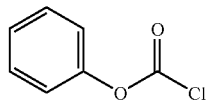

The present invention further relates to a process wherein the compound of formula I is prepared by contacting a compound of formula IV

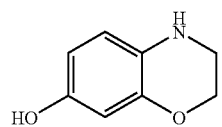

IV with a compound of formula V

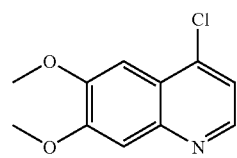

V in the presence of N-methylpyrrolidinone and potassium t-butoxide.

The present invention further relates to a process wherein the compound of formula IV is prepared by contacting a compound of formula VI

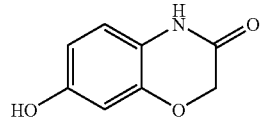

VI with $BH_3$, MeOH and HCl.

The present invention further relates to a process wherein the compound of formula VI is prepared by contacting a compound of formula VII

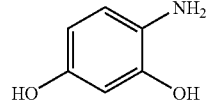

VII with a compound of formula VIII

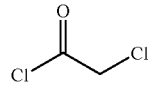

VIII in the presence of potassium carbonate and toluene.

The invention further relates to a compound made by any of the above-described processes.

We have discovered that compound A and salts thereof possess striking unexpected advantages when compared to the structurally closest compound found in the prior art, i.e., reference compound 1. Specifically, compounds of the present invention exhibit remarkably improved in vivo characteristics when compared to reference compound 1.

Compound A and reference compound 1 both potently inhibit VEGF induced proliferation in in vitro cell-based assays as shown below in Table 1 (this assay is described in WO 05/070891).

TABLE 1

| Compound | HUVEC $IC_{50}$ (nM) |
|---|---|
| Reference Compound 1 | 7 |
| Compound A | 2 |

Tables 2 through 6 below describe the results obtained in the rat corneal in vivo model of angiogenesis for (1) reference compound (free base) 1, (2) Compound A (free base), and (3) the hydrochloride salt of Compound A. A VEGF-induced rat corneal angiogenesis assay was performed using the following procedure:

In Life Aspects: Female CD rats weighing approximately 250 grams were randomized into one of six treatment groups. On the day of surgery the rats were temporarily anesthetized using isoflurane. A vertical incision was made on the midline of the cornea and a pocket was created to separate the connective tissue layers of the stroma. The distance between the apex of the pocket and the limbus was approximately 1.8 mm. A presoaked nylon filter disk was inserted to the apex of the pocket (in the case of the control treatment group, the disks were soaked in a buffer containing bovine serum albumin; in the remaining treatment groups, the disks were soaked in buffer containing bovine serum albumin plus human VEGF to induce angiogenesis). The different treatment groups were then dosed daily with either vehicle (Ora Plus™, a commercially available vehicle) or a designated amount of test compound formulated in vehicle.

Study Termination and Analysis: After seven days, the rats were euthanized and the implanted corneas photographed using a Nikon SV-3 Ophthalmic Slit Lamp. Numerical data were generated from the digital images using the Metamorph image analysis system (Universal Imaging). Three endpoints were analyzed on each corneal image: (1) disk placement distance from the limbus, (2) number of vessels intersecting a perpendicular line at the midpoint of the disk placement distance, and (3) blood vessel area, as determined by thresholding and automated pixel counting. Only the number of blood vessels is shown in the tables as this endpoint correlated well with the blood vessel area.

Statistical Analysis: Results were analyzed with the StatView statistical program using one-way ANOVA, followed by Fisher's least significant difference test. Data are presented as mean±SE and P<0.05 was considered significant.

AUC and $ED_{50}$ values were calculated using methods well known in the art.

TABLE 2

Reference Compound 1 (Free Base)

| Treatment Group | # of Rats in Group | Average # of Vessels | Standard Error/p | AUC (ng * hr/ml) |
|---|---|---|---|---|
| Control disc + Vehicle | 7 | 5.7 | 3.0/ NA | |
| VEGF disc + Vehicle | 7 | 19.7 | 4.7/ NA | |
| VEGF disc + 0.01 mg/kg Ref. Cmpd 1 | 7 | 22.0 | 3.9/ NS | 0 |
| VEGF disc + 0.03 mg/kg Ref. Cmpd 1 | 7 | 25.4 | 3.6/ NS | 22.5 |
| VEGF disc + 0.1 mg/kg Ref. Cmpd 1 | 7 | 19.3 | 2.6/ NS | 68.5 |
| VEGF disc + 0.3 mg/kg Ref. Cmpd 1 | 8 | 15.9 | 4.0/ NS | 204.6 |

$ED_{50}$ > 0.3 mg/kg (collected data did not allow for calculation of the $ED_{50}$. Fifty percent reduction in the number of vessels formed did not occur at the highest dose tested).
NS, not significant;
NA, not applicable.

TABLE 3

Compound A (Free Base)

| Treatment Group | # of Rats in Group | Average # of Vessels | Standard Error/p | AUC (ng * hr/ml) |
|---|---|---|---|---|
| Control disc + Vehicle | 7 | 8.6 | 3.8/ NA | |
| VEGF disc + Vehicle | 5 | 37.2 | 4.3/ NA | |
| VEGF disc + 0.03 mg/kg Cmpd A | 8 | 24.5 | 4.4/ =0.0477 | 108.9 |
| VEGF disc + 0.1 mg/kg Cmpd A | 8 | 24.9 | 5.6/ =0.0543 | 203 |
| VEGF disc + 0.3 mg/kg Cmpd A | 7 | 5.4 | 2.1/ <0.0001 | 729.5 |
| VEGF disc + 1.0 mg/kg Cmpd A | 6 | 2.3 | 2.0/ <0.0001 | 2368.9 |

$ED_{50}$ = 0.16 mg/kg
AUC at $ED_{50}$ = 400 ng * hr/ml
NS, not significant;
NA, not applicable.

TABLE 4

Compound A (HCl Salt)
Run # 1

| Treatment Group | # of Rats in Group | Average # of Vessels | Standard Error/p | AUC (ng * hr/ml) |
|---|---|---|---|---|
| Control disc + Vehicle | 8 | 13.1 | 5.9/ NA | |
| VEGF disc + Vehicle | 8 | 26.8 | 4.6/ NA | |
| VEGF disc + 0.03 mg/kg Cmpd A | 6 | 15.3 | 4.7/ NS | 161.7 |
| VEGF disc + 0.1 mg/kg Cmpd A | 8 | 9.3 | 3.9/ =0.0050 | 459.9 |
| VEGF disc + 0.3 mg/kg Cmpd A | 8 | 4.3 | 2.4/ =0.0004 | 1187.9 |
| VEGF disc + 1.0 mg/kg Cmpd A | 8 | 0.4 | 0.4/ <0.0001 | 3638.2 |

$ED_{50}$ = 0.04 mg/kg
AUC at $ED_{50}$ = 200 ng * hr/ml
NS, not significant;
NA, not applicable.

TABLE 5

Compound A (HCl Salt)
Run #2

| Treatment Group | # of Rats in Group | Average # of Vessels | Standard Error/p | AUC (ng * hr/ml) |
|---|---|---|---|---|
| Control disc + Vehicle | 8 | 5.4 | 2.6/ NA | |
| VEGF disc + Vehicle | 8 | 28.3 | 3.3/ NA | |
| VEGF disc + 0.01 mg/kg Cmpd A | 7 | 28.9 | 4.4/ NS | 95.8 |
| VEGF disc + 0.03 mg/kg Cmpd A | 8 | 25.5 | 4.7/ NS | 272.1 |
| VEGF disc + 0.1 mg/kg Cmpd A | 7 | 18.0 | 5.5/ NS | 954.3 |
| VEGF disc + 0.3 mg/kg Cmpd A | 8 | 7.3 | 3.8/ =0.0006 | 3899.5 |

$ED_{50}$ = 0.15 mg/kg
AUC at $ED_{50}$ = 2000 ng * hr/ml
NS, not significant;
NA, not applicable.

TABLE 6

Compound A (HCl Salt)
Run #3

| Treatment Group | # of Rats in Group | Average # of Vessels | Standard Error/p | AUC (ng * hr/ml) |
|---|---|---|---|---|
| Control disc + Vehicle | 7 | 2.7 | 1.0/ NA | |
| VEGF disc + Vehicle | 7 | 24.7 | 2.7/ NA | |
| VEGF disc + 0.01 mg/kg Cmpd A | 8 | 28.4 | 3.6/ NS | 21.8 |
| VEGF disc + 0.03 mg/kg Cmpd A | 8 | 32.0 | 3.3/ NS | 80.2 |
| VEGF disc + 0.1 mg/kg Cmpd A | 8 | 15.4 | 4.1/ =0.0307 | 321.8 |
| VEGF disc + 0.3 mg/kg Cmpd A | 8 | 4.8 | 1.6/ <0.0001 | 677.4 |

$ED_{50}$ = 0.14 mg/kg
AUC at $ED_{50}$ = 338 ng * hr/ml
NS, not significant;
NA, not applicable.

Two major points can be seen from a review of Tables 2 and 3:

(1) Compound A (free base) has a considerably lower $ED_{50}$ than reference compound 1 (free base), 0.16 mpk vs >0.3 mpk; and (2) at the same doses Compound A (free base) has consistently higher exposure across tested doses than that observed for reference compound 1 (free base). This observation correlates with the superior pharmacokinetic profile of compound A in rat compared to the reference compound 1 as indicated in Table 7.

Tables 4-6 illustrate the pharmacological activity of compound A in the rat corneal angiogenesis assay when dosed as an HCl salt. It will be noted that the value of the AUC at $ED_{50}$ in Run # 2 for the hydrochloride salt of Compound A (shown in Table 5) is in obvious disagreement with the data obtained from the two other runs performed with the hydrochloride salt of Compound A as well as the run performed with the free base. The reason for this discrepancy is unknown, and we do not believe that the pharmacokinetic data obtained in Run # 2 (Table 5) are representative of the characteristics of Compound A.

A comparison of the average AUC at the $ED_{50}$ for the 2 other studies conducted with the Compound A HCl salt (i.e., Tables 4 and 6) and the study conducted with the Compound A free base (Table 3) is similar to the value obtained from Run #3 of the HCl salt reported in Table 6 (313 ng*hr/ml vs. 338 ng*hr/ml). Consequently the data from Run #3 are used to represent the efficacy of compound A in the rat corneal angiogenesis model: $ED_{50}$=0.14 mg/kg, AUC at $ED_{50}$=338 ng*hr/ml.

Table 7 provides additional information about the pharmacokinetic profiles of reference compound 1 and Compound A. The data contained in this table was obtained using methods well known in the art.

TABLE 7

| PK Parameter | Ref. Cmpd 1 | Cmpd A |
| --- | --- | --- |
| Rat Clearance (L/h/Kg) | 0.8 | 0.4 |
| Rat Volume of Distribution (L/Kg) | 1.0 | 1.0 |
| Rat I.V. $T_{1/2}$ (h) | 4.73 | 2.1 |
| Rat P.O. $T_{1/2}$ (h) | 2.4 | 2.0 |
| Rat P.O. (2 mpk) % F | 67 | 59 |
| Rat P.O. (2 mpk) $AUC_{0-t}$ (ng * h/ml) | 1705 | 2796 |
| Rat P.O. (2 mpk) $AUC_{0-inf}$ (ng * h/ml) | 1706 | 2813 |
| Rat Liver Microsome (μL/min/mg) | 65 | 45 |
| Human Liver Microsome (μL/min/mg) | 29 | 17 |

Tables 8-14 below provide results obtained in various in vivo xenograft tumor models using Compound A. The procedures used are well known in the art. In general, tumor cell lines of interest are expanded in culture, harvested and injected subcutaneously into 5-8 week old female nude mice (CD1 nu/nu, Charles River Labs) (n=10). Subsequent administration of compound by oral gavage begins anywhere from day 10 to day 28 post tumor cell challenge and continues once a day for the duration of the experiment. Progression of tumor growth is followed by three dimensional caliper measurements and recorded as a function of time. Initial statistical analysis is done by repeated measures analysis of variance (RMANOVA) followed by Scheffe post hoc testing for multiple comparisons. Vehicle alone (Ora-Plus™) was used as the control.

TABLE 8

Effect of Compound A (po, qd) on HT29 Xenografts

| Treatment Group | Tumor Volume ($mm^3$)/Standard Error | | | | |
| --- | --- | --- | --- | --- | --- |
| | day 14 | day 17 | day 20 | day 25 | day 29 |
| Vehicle | 250/17 | 367/34 | 545/51 | 715/69 | 869/91 |
| 3 mpk Cmpd A | 248/16 | 343/38 | 450/38 | 502/48 | 499/52 |
| 10 mpk Cmpd A | 249/16 | 313/22 | 374/35 | 396/39 | 326/30 |
| 30 mpk Cmpd A | 250/17 | 290/13 | 354/26 | 286/23 | 248/19 |

TABLE 9

Effect of Compound A (po, qd) on A431 Xenografts

| Treatment Group | Tumor Volume ($mm^3$)/Standard Error | | | | |
| --- | --- | --- | --- | --- | --- |
| | day 11 | day 14 | day 17 | day 21 | day 24 |
| Vehicle | 266/18 | 366/48 | 518/76 | 734/100 | 1036/79 |
| 1 mpk Cmpd A | 264/16 | 396/21 | 547/37 | 850/75 | 622/47 |
| 3 mpk Cmpd A | 267/19 | 366/37 | 461/30 | 550/44 | 390/20 |
| 10 mpk Cmpd A | 267/18 | 311/30 | 298/33 | 248/30 | 179/23 |

TABLE 10

Effect of Compound A (po, qd) on Large Established Calu-6 Xenografts

| Treatment Group | Tumor Volume ($mm^3$)/Standard Error | | | | | | |
| --- | --- | --- | --- | --- | --- | --- | --- |
| | day 28 | day 32 | day 35 | day 39 | day 42 | day 45 | day 48 |
| 10 mpk Cmpd A | 705/54 | 761/58 | 731/53 | 791/55 | 834/65 | 963/78 | 967/91 |

TABLE 11

Effect of Compound A (po, qd) on Large Established A431 Xenografts

| Treatment Group | Tumor Volume ($mm^3$)/Standard Error | | | | | | | | |
| --- | --- | --- | --- | --- | --- | --- | --- | --- | --- |
| | day 16 | day 20 | day 23 | day 27 | day 30 | day 33 | day 36 | day 47 | day 50 |
| 10 mpk Cmpd A | 633/41 | 539/41 | 388/38 | 335/33 | 274/39 | 236/42 | 240/45 | 226/39 | 217/42 |

TABLE 12

Effect of Compound A (po, qd) on Calu-6 Xenografts

| Treatment Group | Tumor Volume ($mm^3$)/Standard Error | | | | |
| --- | --- | --- | --- | --- | --- |
| | day 17 | day 20 | day 24 | day 28 | day 31 |
| Vehicle | 283/22 | 463/33 | 588/44 | 774/73 | 954/84 |
| 1 mpk Cmpd A | 282/23 | 428/36 | 528/45 | 599/52 | 697/64 |
| 3 mpk Cmpd A | 283/24 | 390/38 | 455/42 | 507 53 | 588/66 |
| 10 mpk Cmpd A | 285/24 | 369/37 | 401/56 | 442/64 | 534/68 |

TABLE 13

Effect of Compound A (po, qd) on A431 (MOA) Xenografts

| Treatment Group | Tumor Volume ($mm^3$)/Standard Error | | | | | | |
| --- | --- | --- | --- | --- | --- | --- | --- |
| | t = 0 | t = 12 hr | day 1 | day 2 | day 3 | day 7 | day 14 |
| Vehicle | 223/24 | 241/25 | 269/29 | 335/42 | 365/41 | 528/49 | 760/80 |
| 10 mpk Cmpd A | | 228/22 | 227/18 | 243/28 | 225/24 | 232/28 | 183/30 |

TABLE 14

Effect of Compound A (po, qd) on A431 (MOA) Xenografts

| Treatment Group | Tumor Volume (mm$^3$)/Standard Error | | | | | | | | |
|---|---|---|---|---|---|---|---|---|---|
| | t = 0 | t = 6 hr | t = 12 hr | day 1 | day 2 | day 3 | day 5 | day 7 | day 14 |
| Vehicle | 351/26 | 359/36 | 370/37 | 385/45 | 404/26 | 435/36 | 599/45 | 760/80 | 597/44 |
| 30 mpk Cmpd A | | 342/23 | 320/21 | 348/31 | 333/33 | 314/28 | 300/19 | 183/30 | 268/21 |

Table 15 below provides the results obtained when Compound A was run in an in vivo bone metastasis model. The procedure used to generate the data is as follows:

Materials and Methods

MDA-231 Luc cells ($1\times10^5$) were injected into the cardiac left ventricle of 4- to 6-week old, female, athymic nude mice (Harlan Sprague Dawley). Positive intra-cardiac injections were confirmed by whole body bioluminescence, and mice were randomized into groups (n=10). Treatment began on day 0 with either of the following 4 treatments: Ora-Plus PO as a vehicle twice daily, recombinant OPG (OPG-Fc) 3.0 mg/kg SC three times weekly, Compound A 30 mg/kg PO twice daily, and Compound A PO once daily. In vivo bioluminescent imaging was performed twice weekly with an IVIS-200 imaging system (Xenogen Corp.). Fifteen minutes prior to imaging, mice were given 150 mg/kg luciferin by i.p. injection. Images were collected and analyzed with Living Image software (Xenogen Corp.), with the region of interest including the femur/tibia region of the hind limbs.

TABLE 15

| Treatment Group | Bioluminescence (photons/sec)/Standard Error | | | | | | |
|---|---|---|---|---|---|---|---|
| | Day 1 | Day 5 | Day 8 | Day 13 | Day 15 | Day 19 | Day 22 |
| Vehicle | 49.94/0.11 | 5.32/0.14 | 5.93/0.18 | 6.80/0.17 | 7.38/0.18 | 7.94/0.18 | 8.60/0.24 |
| OPG-Fc 3 mg/kg | 4.80/0.07 | 5.40/0.11 | 5.61/0.15 | 6.75/0.14 | 7.23/0.14 | 8.00/0.12 | 8.42/0.10 |
| Cmpd A 30 mg/kg BID | 5.20/0.09 | 5.24/0.12 | 6.21/0.10 | 6.87/0.14 | 7.36/0.16 | 7.88/0.14 | 7.95/0.22 |
| Cmpd A 30 mg/kg QD | 5.06/0.08 | 5.43/0.11 | 6.12/0.08 | 7.03/0.16 | 7.55/0.12 | 7.99/0.20 | 8.50/0.15 |

INDICATIONS

Compounds of the present invention would be useful for, but not limited to, the prevention or treatment of angiogenesis related diseases. The compounds of the invention have kinase inhibitory activity, such as VEGFR/KDR inhibitory activity. The compounds of the invention are useful in therapy as antineoplasia agents or to minimize deleterious effects of VEGF.

Compounds of the invention would be useful for the treatment of neoplasia including cancer and metastasis, including, but not limited to: carcinoma such as cancer of the bladder, breast, colon, kidney, liver, lung (including small cell lung cancer), esophagus, gall-bladder, ovary, pancreas, stomach, cervix, thyroid, prostate, and skin (including squamous cell carcinoma); hematopoietic tumors of lymphoid lineage (including leukemia, acute lymphocitic leukemia, acute lymphoblastic leukemia, B-cell lymphoma, T-cell-lymphoma, Hodgkin's lymphoma, non-Hodgkin's lymphoma, hairy cell lymphoma and Burkett's lymphoma); hematopoietic tumors of myeloid lineage (including acute and chronic myelogenous leukemias, myelodysplastic syndrome and promyelocytic leukemia); tumors of mesenchymal origin (including fibrosarcoma and rhabdomyosarcoma, and other sarcomas, e.g. soft tissue and bone); tumors of the central and peripheral nervous system (including astrocytoma, neuroblastoma, glioma and schwannomas); and other tumors (including melanoma, seminoma, teratocarcinoma, osteosarcoma, xenoderoma pigmentosum, keratoctanthoma, thyroid follicular cancer and Kaposi's sarcoma).

Preferably, the compounds are useful for the treatment of neoplasia selected from lung cancer, colon cancer and breast cancer.

The compounds also would be useful for treatment of opthalmological conditions such as corneal graft rejection, ocular neovascularization, retinal neovascularization including neovascularization following injury or infection, diabetic retinopathy, retrolental fibroplasia and neovascular glaucoma; retinal ischemia; vitreous hemorrhage; ulcerative diseases such as gastric ulcer; pathological, but non-malignant, conditions such as hemangiomas, including infantile hemaginomas, angiofibroma of the nasopharynx and avascular necrosis of bone; and disorders of the female reproductive system such as endometriosis. The compounds are also useful for the treatment of edema, and conditions of vascular hyperpermeability.

The compounds of the invention are useful in therapy of proliferative diseases. These compounds can be used for the treatment of an inflammatory rheumatoid or rheumatic disease, especially of manifestations at the locomotor apparatus, such as various inflammatory rheumatoid diseases, especially chronic polyarthritis including rheumatoid arthritis, juvenile arthritis or psoriasis arthropathy; paraneoplastic syndrome or tumor-induced inflammatory diseases, turbid effusions, collagenosis, such as systemic Lupus erythematosus, poly-myositis, dermato-myositis, systemic sclerodermia or mixed collagenosis; postinfectious arthritis (where no living pathogenic organism can be found at or in the affected part of the body), seronegative spondylarthritis, such as spondylitis ankylosans; vasculitis, sarcoidosis, or arthrosis; or further any combinations thereof. An example of an inflammation related disorder is (a) synovial inflammation, for example, synovitis, including any of the particular forms of synovitis, in particular bursal synovitis and purulent synovitis, as far as it is not crystal-induced. Such synovial inflammation may for example, be consequential to or associated with disease, e.g. arthritis, e.g. osteoarthritis, rheumatoid arthritis or arthritis deformans. The present invention is further applicable to the systemic treatment of inflammation, e.g. inflammatory diseases or conditions, of the joints or locomotor apparatus in the region of the tendon insertions and tendon sheaths. Such inflammation may be, for example, consequential to or associated with disease or further (in a broader sense of the invention) with surgical intervention, including, in particular conditions such as insertion endopathy, myofasciale syndrome and tendomyosis. The present invention is further especially applicable to the treatment of inflammation, e.g. inflammatory disease or condition, of connective tissues including dermatomyositis and myositis.

These compounds can be used as active agents against such disease states as arthritis, atherosclerosis, psoriasis, hemangiomas, myocardial angiogenesis, coronary and cerebral collaterals, ischemic limb angiogenesis, wound healing, peptic ulcer *Helicobacter* related diseases, fractures, cat scratch fever, rubeosis, neovascular glaucoma and retinopathies such as those associated with diabetic retinopathy or macular degeneration. In addition, some of these compounds can be used as active agents against solid tumors, malignant ascites, hematopoietic cancers and hyperproliferative disorders such as thyroid hyperplasia (especially Grave's disease), and cysts (such as hypervascularity of ovarian stroma, characteristic of polycystic ovarian syndrome (Stein-Leventhal syndrome)) since such diseases require a proliferation of blood vessel cells for growth and/or metastasis.

Further, some of these compounds can be used as active agents against burns, chronic lung disease, stroke, polyps, anaphylaxis, chronic and allergic inflammation, ovarian hyperstimulation syndrome, brain tumor-associated cerebral edema, high-altitude, trauma or hypoxia induced cerebral or pulmonary edema, ocular and macular edema, ascites, and other diseases where vascular hyperpermeability, effusions, exudates, protein extravasation, or edema is a manifestation of the disease. The compounds will also be useful in treating disorders in which protein extravasation leads to the deposition of fibrin and extracellular matrix, promoting stromal proliferation (e.g. fibrosis, cirrhosis and carpal tunnel syndrome).

The compounds of the present invention are also useful in the treatment of ulcers including bacterial, fungal, Mooren ulcers and ulcerative colitis.

The compounds of the present invention are also useful in the treatment of conditions wherein undesired angiogenesis, edema, or stromal deposition occurs in viral infections such as Herpes simplex, Herpes Zoster, AIDS, Kaposi's sarcoma, protozoan infections and toxoplasmosis, following trauma, radiation, stroke, endometriosis, ovarian hyperstimulation syndrome, systemic lupus, sarcoidosis, synovitis, Crohn's disease, sickle cell anemia, Lyme disease, pemphigoid, Paget's disease, hyperviscosity syndrome, Osler-Weber-Rendu disease, chronic inflammation, chronic occlusive pulmonary disease, asthma, and inflammatory rheumatoid or rheumatic disease. The compounds are also useful in the reduction of sub-cutaneous fat and for the treatment of obesity.

The compounds of the present invention are also useful in the treatment of ocular conditions such as ocular and macular edema, ocular neovascular disease, scleritis, radial keratotomy, uveitis, vitritis, myopia, optic pits, chronic retinal detachment, post-laser complications, glaucoma, conjunctivitis, Stargardt's disease and Eales disease in addition to retinopathy and macular degeneration.

The compounds of the present invention are also useful in the treatment of cancer related indications such as solid tumors, sarcomas (especially Ewing's sarcoma and osteosarcoma), retinoblastoma, rhabdomyosarcomas, neuroblastoma, hematopoietic malignancies, including leukemia and lymphoma, tumor-induced pleural or pericardial effusions, and malignant ascites.

As used herein, the compounds of the present invention include the pharmaceutically acceptable derivatives thereof.

Where the plural form is used for compounds, salts, and the like, this is taken to mean also a sindle compound, salt and the like.

DEFINITIONS

"Angiogenesis" is defined as any alteration of an existing vascular bed or the formation of new vasculature, which benefits tissue perfasion. This includes the formation of new vessels by sprouting of endothelial cells from existing blood vessels or the remodeling of existing vessels to alter size, maturity, direction or flow properties to improve blood perfusion of tissue.

The terms "cancer" and "cancerous" when used herein refer to or describe the physiological condition in mammals that is typically characterized by unregulated cell growth. Examples of cancer include but are not limited to, carcinoma, lymphoma, sarcoma, blastoma and leukemia. More particular examples of such cancers include squamous cell carcinoma, lung cancer, pancreatic cancer, cervical cancer, bladder cancer, hepatoma, breast cancer, colon carcinoma, and head and neck cancer. The terms "treating," "treatment," and "therapy" as used herein refer to curative therapy, prophylactic therapy, and preventative therapy.

The term "mammal" as used herein refers to any mammal classified as a mammal, including humans, cows, horses, dogs and cats. In a preferred embodiment of the invention, the mammal is a human.

The term "treatment" (or "treating") includes therapeutic treatment as well as prophylactic treatment (either preventing the onset of disorders altogether or delaying the onset of a pre-clinically evident stage of disorders in individuals).

The phrase "therapeutically-effective" is intended to qualify the amount of each agent, which will achieve the goal of improvement in disorder severity and the frequency of incidence over treatment of each agent by itself, while avoiding adverse side effects typically associated with alternative therapies. For example, effective neoplastic therapeutic agents prolong the survivability of the patient, inhibit the rapidly proliferating cell growth associated with the neoplasm, or effect a regression of the neoplasm.

The term "halogen" (or "halo") means fluorine, chlorine, bromine or iodine atoms.

The term "aryl", alone or in combination, means a carbocyclic aromatic system containing one or two rings wherein such rings may be attached together in a fused manner. The term "aryl" embraces aromatic radicals such as phenyl, naphthyl, indenyl, tetrahydronaphthyl, and indanyl. More preferred aryl is phenyl. Said "aryl" group may have 1 or more substituents such as lower alkyl, hydroxyl, halo, haloalkyl, nitro, cyano, alkoxy, lower alkylamino, and the like. Phenyl substituted with —O—CH$_2$—O— forms the aryl benzodioxolyl substituent.

The term "heteroaryl" denotes aryl ring systems that contain one or more heteroatoms selected from the group O, N and S, wherein the ring nitrogen and sulfur atom(s) are optionally oxidized, and nitrogen atom(s) are optionally quarternized. Examples include unsaturated 5 to 6 membered heteromonocyclyl group containing 1 to 4 nitrogen atoms, for example, pyrrolyl, imidazolyl, pyrazolyl, 2-pyridyl, 3-pyridyl, 4-pyridyl, pyrimidyl, pyrazinyl, pyridazinyl, triazolyl [e.g., 4H-1,2,4-triazolyl, 1H-1,2,3-triazolyl, 2H-1,2,3-triazolyl]; unsaturated 5- to 6-membered heteromonocyclic group containing an oxygen atom, for example, pyranyl, 2-furyl, 3-furyl, etc.; unsaturated 5 to 6-membered heteromonocyclic group containing a sulfur atom, for example, 2-thienyl, 3-thienyl, etc.; unsaturated 5- to 6-membered heteromonocyclic group containing 1 to 2 oxygen atoms and 1 to 3 nitrogen atoms, for example, oxazolyl, isoxazolyl, oxadiazolyl [e.g., 1,2,4-oxadiazolyl, 1,3,4-oxadiazolyl, 1,2,5-oxadiazolyl]; unsaturated 5 to 6-membered heteromonocyclic group containing 1 to 2 sulfur atoms and 1 to 3 nitrogen atoms, for example, thiazolyl, thiadiazolyl [e.g., 1,2,4-thiadiazolyl, 1,3,4-thiadiazolyl, 1,2,5-thiadiazolyl]. Said "heteroaryl" group may have 1 or more substituents such as lower alkyl, hydroxyl, halo, haloalkyl, nitro, cyano, alkoxy, lower alkylamino, and the like.

The term "comprising" is meant to be open ended, including the indicated component but not excluding other elements.

The term "active metabolite" as used herein refers any of the following compounds:

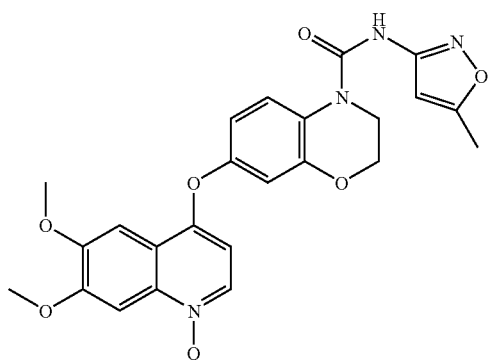

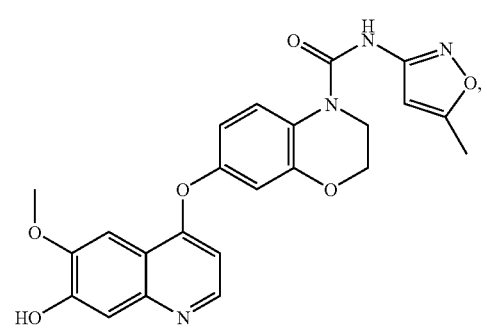

-continued

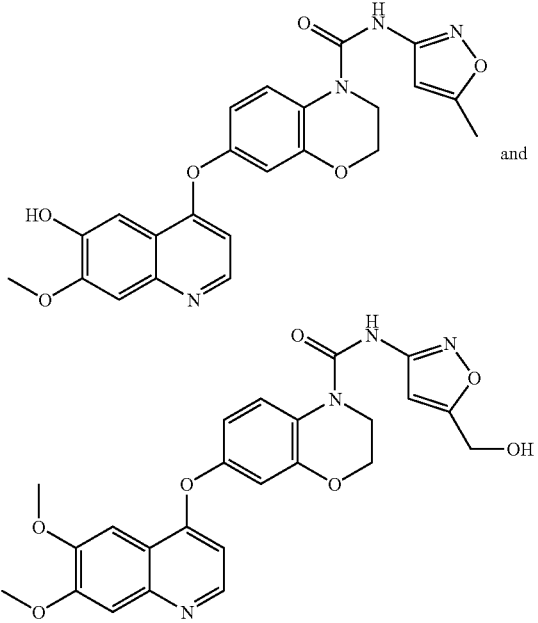

The present invention also comprises the use of a compound of the invention, or pharmaceutically acceptable salt thereof, in the manufacture of a medicament for the treatment either acutely or chronically of an angiogenesis mediated disease state, including those described previously. The compounds of the present invention are useful in the manufacture of an anti-cancer medicament.

The present invention comprises a pharmaceutical composition comprising a therapeutically effective amount of a compound of the current invention in association with a least one pharmaceutically acceptable carrier, adjuvant or diluent.

The present invention also comprises a method of treating angiogenesis related disorders in a subject having or susceptible to such disorder, the method comprising treating the subject with a therapeutically effective amount of a compound of the current invention.

COMBINATIONS

While the compounds of the invention can be administered as the sole active pharmaceutical agent, they can also be used in combination with one or more compounds of the invention or other agents. When administered as a combination, the therapeutic agents can be formulated as separate compositions that are administered at the same time or sequentially at different times, or the therapeutic agents can be given as a single composition.

The phrase "co-therapy" (or "combination-therapy"), in defining use of a compound of the present invention and another pharmaceutical agent, is intended to embrace administration of each agent in a sequential manner in a regimen that will provide beneficial effects of the drug combination, and is intended as well to embrace co-administration of these agents in a substantially simultaneous manner, such as in a single capsule having a fixed ratio of these active agents or in multiple, separate capsules for each agent.

Specifically, the administration of compounds of the present invention may be in conjunction with additional therapies known to those skilled in the art in the prevention or treatment of neoplasia, such as with radiation therapy or with cytostatic or cytotoxic agents.

If formulated as a fixed dose, such combination products employ the compounds of this invention within the accepted dosage ranges. Compounds of the current invention may also be administered sequentially with known anticancer or cytotoxic agents when a combination formulation is inappropriate. The invention is not limited in the sequence of administration; compounds of the invention may be administered either prior to, simultaneously with or after administration of the known anticancer or cytotoxic agent.

Currently, standard treatment of primary tumors consists of surgical excision followed by either radiation or IV administered chemotherapy. The typical chemotherapy regime consists of either DNA alkylating agents, DNA intercalating agents, CDK inhibitors, or microtubule poisons. The chemotherapy doses used are just below the maximal tolerated dose and therefore dose limiting toxicities typically include, nausea, vomiting, diarrhea, hair loss, neutropenia and the like.

There are large numbers of antineoplastic agents available in commercial use, in clinical evaluation and in pre-clinical development, which would be selected for treatment of neoplasia by combination drug chemotherapy. Such antineoplastic agents fall into several major categories, namely, antibiotic-type agents, alkylating agents, antimetabolite agents, hormonal agents, immunological agents, interferon-type agents and a category of miscellaneous agents.

A first family of antineoplastic agents, which may be used in combination with compounds of the present invention, consists of antimetabolite-type/thymidilate synthase inhibitor antineoplastic agents. Suitable antimetabolite antineoplastic agents may be selected from but not limited to the group consisting of 5-FU-fibrinogen, acanthifolic acid, aminothiadiazole, brequinar sodium, carmofur, Ciba-Geigy CGP-30694, cyclopentyl cytosine, cytarabine phosphate stearate, cytarabine conjugates, Lilly DATHF, Merrel Dow DDFC, dezaguanine, dideoxycytidine, dideoxyguanosine, didox, Yoshitomi DMDC, doxifluridine, Wellcome EHNA, Merck & Co. EX-015, fazarabine, floxuridine, fludarabine phosphate, 5-fluorouracil, N-(2'-furanidyl)-5-fluorouracil, Daiichi Seiyaku FO-152, isopropyl pyrrolizine, Lilly LY-188011, Lilly LY-264618, methobenzaprim, methotrexate, Wellcome MZPES, norspermidine, NCI NSC-127716, NCI NSC-264880, NCI NSC-39661, NCI NSC-612567, Warner-Lambert PALA, pentostatin, piritrexim, plicamycin, Asahi Chemical PL-AC, Takeda TAC-788, thioguanine, tiazofurin, Erbamont TIF, trimetrexate, tyrosine kinase inhibitors, Taiho UFT and uricytin.

A second family of antineoplastic agents, which may be used in combination with compounds of the present invention, consists of alkylating-type antineoplastic agents. Suitable alkylating-type antineoplastic agents may be selected from but not limited to the group consisting of Shionogi 254-S, aldo-phosphamide analogues, altretamine, anaxirone, Boehringer Mannheim BBR-2207, bestrabucil, budotitane, Wakunaga CA-102, carboplatin, carmustine, Chinoin-139, Chinoin-153, chlorambucil, cisplatin, cyclophosphamide, American Cyanamid CL-286558, Sanofi CY-233, cyplatate, Degussa D-19-384, Sumimoto DACHP(Myr)2, diphenylspiromustine, diplatinum cytostatic, Erba distamycin derivatives, Chugai DWA-2114R, ITI E09, elmustine, Erbamont FCE-24517, estramustine phosphate sodium, fotemustine, Unimed G-6-M, Chinoin GYKI-17230, hepsul-fam, ifosfamide, iproplatin, lomustine, mafosfamide, mitolactol, Nippon Kayaku NK-121, NCI NSC-264395, NCI NSC-342215, oxaliplatin, Upjohn PCNU, prednimustine, Proter PTT-119, ranimustine, semustine, SmithKline SK&F-101772, Yakult Honsha SN-22, spiromus-tine, Tanabe Seiyaku TA-077, tauromustine, temozolomide, teroxirone, tetraplatin and trimelamol.

A third family of antineoplastic agents which may be used in combination with compounds of the present invention consists of antibiotic-type antineoplastic agents. Suitable antibiotic-type antineoplastic agents may be selected from but not limited to the group consisting of Taiho 4181-A, aclarubicin, actinomycin D, actinoplanone, Erbamont ADR-456, aeroplysinin derivative, Ajinomoto AN-201-II, Ajinomoto AN-3, Nippon Soda anisomycins, anthracycline, azino-mycin-A, bisucaberin, Bristol-Myers BL-6859, Bristol-Myers BMY-25067, Bristol-Myers BMY-25551, Bristol-Myers BMY-26605, Bristol-Myers BMY-27557, Bristol-Myers BMY-28438, bleomycin sulfate, bryostatin-1, Taiho C-1027, calichemycin, chromoximycin, dactinomycin, daunorubicin, Kyowa Hakko DC-102, Kyowa Hakko DC-79, Kyowa Hakko DC-88A, Kyowa Hakko DC89-A1, Kyowa Hakko DC92-B, ditrisarubicin B, Shionogi DOB-41, doxorubicin, doxorubicin-fibrinogen, elsamicin-A, epirubicin, erbstatin, esorubicin, esperamicin-A1, esperamicin-Alb, Erbamont FCE-21954, Fujisawa FK-973, fostriecin, Fujisawa FR-900482, glidobactin, gregatin-A, grincamycin, herbimycin, idarubicin, illudins, kazusamycin, kesarirhodins, Kyowa Hakko KM-5539, Kirin Brewery KRN-8602, Kyowa Hakko KT-5432, Kyowa Hakko KT-5594, Kyowa Hakko KT-6149, American Cyanamid LL-D49194, Meiji Seika ME 2303, menogaril, mitomycin, mitoxantrone, SmithKline M-TAG, neoenactin, Nippon Kayaku NK-313, Nippon Kayaku NKT-01, SR1 International NSC-357704, oxalysine, oxaunomycin, peplomycin, pilatin, pirarubicin, porothramycin, pyrindanycin A, Tobishi RA-I, rapamycin, rhizoxin, rodorubicin, sibanomicin, siwenmycin, Sumitomo SM-5887, Snow Brand SN-706, Snow Brand SN-07, sorangicin-A, sparsomycin, SS Pharmaceutical SS-21020, SS Pharmaceutical SS-7313B, SS Pharmaceutical SS-9816B, steffimycin B, Taiho 4181-2, talisomycin, Takeda TAN-868A, terpentecin, thrazine, tricrozarin A, Upjohn U-73975, Kyowa Hakko UCN-10028A, Fujisawa WF-3405, Yoshitomi Y-25024 and zorubicin.

A fourth family of antineoplastic agents which may be used in combination with compounds of the present invention consists of a miscellaneous family of antineoplastic agents, including tubulin interacting agents, topoisomerase II inhibitors, topoisomerase I inhibitors and hormonal agents, selected from but not limited to the group consisting of α-carotene, α-difluoromethyl-arginine, acitretin, Biotec AD-5, Kyorin AHC-52, alstonine, amonafide, amphethinile, amsacrine, Angiostat, ankinomycin, anti-neoplaston A10, antineoplaston A2, antineoplaston A3, antineoplaston A5, antineoplaston AS2-1, Henkel APD, aphidicolin glycinate, asparaginase, Avarol, baccharin, batracylin, benfluoron, benzotript, Ipsen-Beaufour BIM-23015, bisantrene, Bristol-Myers BMY-40481, Vestar boron-10, bromofosfamide, Wellcome BW-502, Wellcome BW-773, caracemide, carmethizole hydrochloride, Ajinomoto CDAF, chlorsulfaquinoxalone, Chemes CHX-2053, Chemex CHX-100, Warner-Lambert CI-921, Warner-Lambert CI-937, Warner-Lambert CI-941, Warner-Lambert CI-958, clanfenur, claviridenone, ICN compound 1259, ICN compound 4711, Contracan, Yakult Honsha CPT-11, crisnatol, curaderm, cytochalasin B, cytarabine, cytocytin, Merz D-609, DABIS maleate, dacarbazine, datelliptinium, didemnin-B, dihaematoporphyrin ether, dihydrolenperone, dinaline, distamycin, Toyo Pharmar DM-341, Toyo Pharmar DM-75, Daiichi Seiyaku DN-9693, docetaxel elliprabin, ellipitinium acetate, Tsumura EPMTC, the epothilones, ergotamine, etoposide, etretinate, fenretinide, Fujisawa FR-57704, gallium nitrate, genkwadaphnin, Chugai GLA-43, Glaxo GR-63178, grifolan NMF-5N, hexadecylphosphocholine, Green Cross HO-221, homoharringtonine, hydroxyurea, BTG ICRF-187, ilmofosine, isoglutamine, isotretinoin, Otsuka JI-36, Ramot K-477, Otsuak K-76COONa, Kureha Chemical K-AM, MECT Corp KI-8110, American Cyanamid L-623, leukoregulin, lonidamine, Lundbeck LU-23-112, Lilly LY-186641, NCI (US) MAP, marycin, Merrel Dow MDL-27048, Medco MEDR-340, merbarone, merocyanlne derivatives, methylanilinoacridine, Molecular Genetics MGI-136, minactivin, mitonafide, mitoquidone mopidamol, motretinide, Zenyaku Kogyo MST-16, N-(retinoyl)amino acids, Nisshin Flour Milling N-021, N-acylated-dehydroalanines, nafazatrom, Taisho NCU-190, nocodazole derivative, Normosang, NCI NSC-145813, NCI NSC-361456, NCI NSC-604782, NCI NSC-95580, ocreotide, Ono ONO-112, oquizanocine, Akzo Org-10172, paclitaxel, pancratistatin, pazelliptine, Warner-Lambert PD-111707, Warner-Lambert PD-115934, Warner-Lambert PD-131141, Pierre Fabre PE-1001, ICRT peptide D, piroxantrone, polyhaematoporphyrin, polypreic acid, Efamol porphyrin, probimane, procarbazine, proglumide, Invitron protease nexin I, Tobishi RA-700, razoxane, Sapporo Breweries RBS, restrictin-P, retelliptine, retinoic acid, Rhone-Poulenc RP-49532, Rhone-Poulenc RP-56976, SmithKline SK&F-104864, Sumitomo SM-108, Kuraray SMANCS, SeaPharm SP-10094, spatol, spirocyclopropane derivatives, spirogermanium, Unimed, SS Pharmaceutical SS-554, strypoldinone, Stypoldione, Suntory SUN 0237, Suntory SUN 2071, superoxide dismutase, Toyama T-506, Toyama T-680, taxol, Teijin TEI-0303, teniposide, thaliblastine, Eastman Kodak TJB-29, tocotrienol, topotecan, Topostin, Teijin TT-82, Kyowa Hakko UCN-01, Kyowa Hakko UCN-1028, ukrain, Eastman Kodak USB-006, vinblastine sulfate, vincristine, vindesine, vinestramide, vinorelbine, vintriptol, vinzolidine, withanolides and Yamanouchi YM-534.

Alternatively, the present compounds may also be used in co-therapies with other anti-neoplastic agents, such as acemannan, aclarubicin, aldesleukin, alemtuzumab, alitretinoin, altretamine, amifostine, aminolevulinic acid, amrubicin, amsacrine, anagrelide, anastrozole, ANCER, ancestim, ARGLABIN, arsenic trioxide, BAM 002 (Novelos), bexarotene, bicalutamide, broxuridine, capecitabine, celmoleukin, cetrorelix, cladribine, clotrimazole, cytarabine ocfosfate, DA 3030 (Dong-A), daclizumab, denileukin diftitox, deslorelin, dexrazoxane, dilazep, docetaxel, docosanol, doxercalciferol, doxifluridine, doxorubicin, bromocriptine, cammustine, cytarabine, fluorouracil, HIT diclofenac, interferon alfa, daunorubicin, doxorubicin, tretinoin, edelfosine, edrecolomab, eflornithine, emitefur, epirubicin, epoetin beta, etoposide phosphate, exemestane, exisulind, fadrozole, filgrastim, finasteride, fludarabine phosphate, formestane, fotemustine, gallium nitrate, gemcitabine, gemtuzumab zogamicin, gimeracil/oteracil/tegafur combination, glycopine, goserelin, heptaplatin, human chorionic gonadotropin, human fetal alpha fetoprotein, ibandronic acid, idarubicin, (imiquimod, interferon alfa, interferon alfa, natural, interferon alfa-2, interferon alfa-2a, interferon alfa-2b, interferon alfa-N1, interferon alfa-n3, interferon alfacon-1, interferon alpha, natural, interferon beta, interferon beta-1a, interferon beta-1b, interferon gamma, natural interferon gamma-1a, interferon gamma-1b, interleukin-1 beta, iobenguane, irinotecan, irsogladine, lanreotide, LC 9018 (Yakult), leflunomide, lenograstim, lentinan sulfate, letrozole, leukocyte alpha interferon, leuprorelin, levamisole+fluorouracil, liarozole, lobaplatin, lonidamine, lovastatin, masoprocol, melarsoprol, metoclopramide, mifepristone, miltefosine, mirimostim, mismatched double stranded RNA, mitoguazone, mitolactol, mitoxantrone, molgramostim, nafarelin, naloxone+pentazocine, nartograstim, nedaplatin, nilutamide, noscapine, novel erythropoiesis stimulating protein, NSC 631570 octreotide, oprelvekin, osaterone, oxaliplatin, paclitaxel, pamidronic acid, pegaspargase, peginterferon alfa-2b, pentosan polysulfate sodium, pentostatin, picibanil, pirarubicin, rabbit antithymocyte polyclonal antibody, polyethylene glycol interferon alfa-2a, porfimer sodium, raloxifene, raltitrexed, rasburicase, rhenium Re 186 etidronate, RII retinamide, rituximab, romurtide, samarium (153 Sm) lexidronam, sargramostim, sizofuran, sobuzoxane, sonermin, strontium-89 chloride, suramin, tasonermin, tazarotene, tegafur, temoporfin, temozolomide, teniposide, tetrachlorodecaoxide, thalidomide, thymalfasin, thyrotropin alfa, topotecan, toremifene, tositumomab-iodine 131, trastuzumab, treosulfan, tretinoin, trilostane, trimetrexate, triptorelin, tumor necrosis factor alpha, natural, ubenimex, bladder cancer vaccine, Maruyama vaccine, melanoma lysate vaccine, valrubicin, verteporfin, vinorelbine, VIRULIZIN, zinostatin stimalamer, or zoledronic acid; abarelix; AE 941 (Aeterna), ambamustine, antisense oligonucleotide, bcl-2 (Genta), APC 8015 (Dendreon), cetuximab, decitabine, dexaminoglutethimide, diaziquone, EL 532 (Elan), EM 800 (Endorecherche), eniluracil, etanidazole, fenretinide, filgrastim SDOI (Amgen), fulvestrant, galocitabine, gastrin 17 immunogen, HLA-B7 gene therapy (Vical), granulocyte macrophage colony stimulating factor, histamine dihydrochloride, ibritumomab tiuxetan, ilomastat, IM 862 (Cytran), interleukin-2, iproxifene, LDI 200 (Milkhaus), leridistim, lintuzumab, CA 125 MAb (Biomira), cancer MAb (Japan Pharmaceutical Development), HER-2 and Fc MAb (Medarex), idiotypic 105AD7 MAb (CRC Technology), idiotypic CEA MAb (Trilex), LYM-1-iodine 131 MAb (Techniclone), polymorphic epithelial mucin-yttrium 90 MAb (Antisoma), marimastat, menogaril, mitumomab, motexafin gadolinium, MX 6 (Galderma), nelarabine, nolatrexed, P 30 protein, pegvisomant, pemetrexed, porfiromycin, prinomastat, RL 0903 (Shire), rubitecan, satraplatin, sodium phenylacetate, sparfosic acid, SRL 172 (SR Pharma), SU 5416 (SUGEN), TA 077 (Tanabe), tetrathiomolybdate, thaliblastine, thrombopoietin, tin ethyl etiopurpurin, tirapazamine, cancer vaccine (Biomira), melanoma vaccine (New York University), melanoma vaccine (Sloan Kettering Institute), melanoma oncolysate vaccine (New York Medical College), viral melanoma cell lysates vaccine (Royal Newcastle Hospital), or valspodar.

Alternatively, the present compounds may also be used in co-therapies with VEGFR inhibitors including N-(4-chlorophenyl)-4-(4-pyridinylmethyl)-1-phthalazinamine;

4-[4-[[[[4-chloro-3-(trifluoromethyl)phenyl]amino]carbonyl]amino]phenoxy]-N-methyl-2-pyridinecarboxamide;

N-[2-(diethylamino)ethyl]-5-[(5-fluoro-1,2-dihydro-2-oxo-3H-indol-3-ylidene)methyl]-2,4-dimethyl-1H-pyrrole-3-carboxamide;

3-[(4-bromo-2,6-difluorophenyl)methoxy]-5-[[[[4-(1-pyrrolidinyl)butyl]amino]carbonyl]amino]-4-isothiazolecarboxamide;

N-(4-bromo-2-fluorophenyl)-6-methoxy-7-[(1-methyl-4-piperidinyl)methoxy]-4-quinazolinamine;

3-[5,6,7,13-tetrahydro-9-[(1-methylethoxy)methyl]-5-oxo-12H-indeno[2,1-a]pyrrolo[3,4-c]carbazol-12-yl]propyl ester N,N-dimethyl-glycine;

N-[5-[[[5-(1,1-dimethylethyl)-2-oxazolyl]methyl]thio]-2-thiazolyl]-4-piperidinecarboxamide;

N-[3-chloro-4-[(3-fluorophenyl)methoxy]phenyl]-6-[5-[[[2-(methylsulfonyl)ethyl]amino]methyl]-2-furanyl]-4-quinazolinamine 4-[(4-Methyl-1-piperazinyl)methyl]-N-[4-methyl-3-[[4-(3-pyridinyl)-2-pyrimidinyl]amino]-phenyl]benzamide N-(3-chloro-4-fluorophenyl)-7-methoxy-6-[3-(4-morpholinyl)propoxy]-4-quinazolinamine N-(3-ethynylphenyl)-6,7-bis(2-methoxyethoxy)-4-quinazolinamine N-(3-((((2R)-1-methyl-2-pyrrolidinyl)methyl)oxy)-5-(trifluoromethyl)phenyl)-2-((3-(1,3-oxazol-5-yl)phenyl)amino)-3-pyridinecarboxamide;

2-(((4-fluorophenyl)methyl)amino)-N-(3-((((2R)-1-methyl-2-pyrrolidinyl)methyl)oxy)-5-(trifluoromethyl)phenyl)-3-pyridinecarboxamide;

N-[3-(Azetidin-3-ylmethoxy)-5-trifluoromethyl-phenyl]-2-(4-fluoro-benzylamino)-nicotinamide.

6-fluoro-N-(4-(1-methylethyl)phenyl)-2-((4-pyridinylmethyl)amino)-3-pyridinecarboxamide;

2-((4-pyridinylmethyl)amino)-N-(3-(((2S)-2-pyrrolidinylmethyl)oxy)-5-(trifluoromethyl)phenyl)-3-pyridinecarboxamide;

N-(3-(1,1-dimethylethyl)-1H-pyrazol-5-yl)-2-((4-pyridinylmethyl)amino)-3-pyridinecarboxamide;

N-(3,3-dimethyl-2,3-dihydro-1-benzofuran-6-yl)-2-((4-pyridinylmethyl)amino)-3-pyridinecarboxamide;

N-(3-((((2S)-1-methyl-2-pyrrolidinyl)methyl)oxy)-5-(trifluoromethyl)phenyl)-2-((4-pyridinylmethyl)amino)-3-pyridinecarboxamide;

2-((4-pyridinylmethyl)amino)-N-(3-((2-(1-pyrrolidinyl)ethyl)oxy)-4-(trifluoromethyl)phenyl)-3-pyridinecarboxamide;

N-(3,3-dimethyl-2,3-dihydro-1H-indol-6-yl)-2-((4-pyridinylmethyl)amino)-3-pyridinecarboxamide;

N-(4-(pentafluoroethyl)-3-(((2S)-2-pyrrolidinylmethyl)oxy)phenyl)-2-((4-pyridinylmethyl)amino)-3-pyridinecarboxamide;

N-(3-((3-azetidinylmethyl)oxy)-5-(trifluoromethyl)phenyl)-2-((4-pyridinylmethyl)amino)-3-pyridinecarboxamide;

N-(3-(4-piperidinyloxy)-5-(trifluoromethyl)phenyl)-2-((2-(3-pyridinyl)ethyl)amino)-3-pyridinecarboxamide;

N-(4,4-dimethyl-1,2,3,4-tetrahydro-isoquinolin-7-yl)-2-(1H-indazol-6-ylamino)-nicotinamide;

2-(1H-indazol-6-ylamino)-N-[3-(1-methylpyrrolidin-2-ylmethoxy)-5-trifluoromethyl-phenyl]-nicotinamide;

N-[1-(2-dimethylamino-acetyl)-3,3-dimethyl-2,3-dihydro-1H-indol-6-yl]-2-(1H-indazol-6-ylamino)-nicotinamide;

2-(1H-indazol-6-ylamino)-N-[3-(pyrrolidin-2-ylmethoxy)-5-trifluoromethyl-phenyl]-nicotinamide;

N-(1-acetyl-3,3-dimethyl-2,3-dihydro-1H-indol-6-yl)-2-(1H-indazol-6-ylamino)-nicotinamide;

N-(4,4-dimethyl-1-oxo-1,2,3,4-tetrahydro-isoquinolin-7-yl)-2-(1H-indazol-6-ylamino)-nicotinamide;

N-[4-(tert-butyl)-3-(3-piperidylpropyl)phenyl][2-(1H-indazol-6-ylamino)(3-pyridyl)]carboxamide;

N-[5-(tert-butyl)isoxazol-3-yl][2-(1H-indazol-6-ylamino)(3-pyridyl)]carboxamide; and N-[4-(tert-butyl)phenyl][2-(1H-indazol-6-ylamino)(3-pyridyl)]carboxamide.

Other compounds described in the following patents and patent applications can be used in combination therapy: U.S. Pat. No. 6,258,812, US 2003/0105091, WO 01/37820, U.S. Pat. No. 6,235,764, WO 01/32651, U.S. Pat. No. 6,630,500, U.S. Pat. No. 6,515,004, U.S. Pat. No. 6,713,485, U.S. Pat. No. 5,521,184, U.S. Pat. No. 5,770,599, U.S. Pat. No. 5,747,498, WO 02/68406, WO 02/66470, WO 02/55501, WO 04/05279, WO 04/07481, WO 04/07458, WO 04/09784, WO 02/59110, WO 99/45009, WO 00/59509, WO 99/61422, U.S. Pat. No. 5,990,141, WO 00/12089 and WO 00/02871.

In some embodiments, the combination comprises a composition of the present invention in combination with at least one anti-angiogenic agent. Agents are inclusive of, but not limited to, in vitro synthetically prepared chemical compositions, antibodies, antigen binding regions, radionuclides, and combinations and conjugates thereof. An agent can be an agonist, antagonist, allosteric modulator, toxin or, more generally, may act to inhibit or stimulate its target (e.g., receptor or enzyme activation or inhibition), and thereby promote cell death or arrest cell growth.

Exemplary anti-tumor agents include HERCEPTIN™ (trastuzumab), which may be used to treat breast cancer and other forms of cancer, and RITUXAN™ (rituximab), ZEVALIN™ (ibritumomab tiuxetan), and LYMPHOCIDE™ (epratuzumab), which may be used to treat non-Hodgkin's lymphoma and other forms of cancer, GLEEVAC™ which may be used to treat chronic myeloid leukemia and gastrointestinal stromal tumors, and BEXXAR™ (iodine 131 tositumomab) which may be used for treatment of non-Hodgkins's lymphoma.

Exemplary anti-angiogenic agents include KDR (kinase domain receptor) inhibitory agents (e.g., antibodies and antigen binding regions that specifically bind to the kinase domain receptor), anti-VEGF agents (e.g., antibodies or antigen binding regions that specifically bind VEGF, or soluble VEGF receptors or a ligand binding region thereof) such as AVASTIN™ or VEGF-TRAP™, and anti-VEGF receptor agents (e.g., antibodies or antigen binding regions that specifically bind thereto), EGFR inhibitory agents (e.g., antibodies or antigen binding regions that specifically bind thereto) such as ERBITUX™ (IMC-C225), and VECTIBIX™ (panitumumab) IRESSA™ (gefitinib), TARCEVA™ (erlotinib), anti-Ang1 and anti-Ang2 agents (e.g., antibodies or antigen binding regions specifically binding thereto or to their receptors, e.g., Tie2/Tek), and anti-Tie2 kinase inhibitory agents. The pharmaceutical compositions of the present invention can also include one or more agents (e.g., antibodies, antigen binding regions, or soluble receptors) that specifically bind and inhibit the activity of growth factors, such as antagonists of hepatocyte growth factor (HGF, also known as Scatter Factor), and antibodies or antigen binding regions that specifically bind its receptor "c-Met" as well as small molecules inhibitors of the c-Met kinase activity.

Other anti-angiogenic agents include Campath, IL-8, B-FGF, Tek antagonists (Ceretti et al., US Publication No. 2003/0162712; U.S. Pat. No. 6,413,932), anti-TWEAK agents (e.g., specifically binding antibodies or antigen binding regions, or soluble TWEAK receptor antagonists; see, Wiley, U.S. Pat. No. 6,727,225), ADAM distintegrin domain to antagonize the binding of integrin to its ligands (Fanslow et al., US Publication No. 2002/0042368), specifically binding anti-eph receptor and/or anti-ephrin antibodies or antigen binding regions (U.S. Pat. Nos. 5,981,245; 5,728,813; 5,969,110; 6,596,852; 6,232,447; 6,057,124 and patent family members thereof), and anti-PDGF-BB antagonists (e.g., specifically binding antibodies or antigen binding regions) as well as antibodies or antigen binding regions specifically binding to PDGF-BB ligands, and PDGFR kinase inhibitory agents (e.g., antibodies or antigen binding regions that specifically bind thereto).

Additional anti-angiogenic/anti-tumor agents include: SD-7784 (Pfizer, USA); cilengitide. (Merck KGaA, Germany, EPO 770622); pegaptanib octasodium, (Gilead Sciences, USA); Alphastatin, (BioActa, UK); M-PGA, (Celgene, USA, U.S. Pat. No. 5,712,291); ilomastat, (Arriva, USA, U.S. Pat. No. 5,892,112); emaxanib, (Pfizer, USA, U.S. Pat. No. 5,792,783); vatalanib, (Novartis, Switzerland); 2-methoxyestradiol, (EntreMed, USA); TLC ELL-12, (Elan, Ireland); anecortave acetate, (Alcon, USA); alpha-D148 Mab, (Amgen, USA); CEP-7055, (Cephalon, USA); anti-Vn Mab, (Crucell, Netherlands) DAC:antiangiogenic, (ConjuChem, Canada); Angiocidin, (InKine Pharmaceutical, USA); KM-2550, (Kyowa Hakko, Japan); SU-0879, (Pfizer, USA); CGP-79787, (Novartis, Switzerland, EP 970070); ARGENT technology, (Ariad, USA); YIGSR-Stealth, (Johnson & Johnson, USA); fibrinogen-E fragment, (BioActa, UK); angiogenesis inhibitor, (Trigen, UK); TBC-1635, (Encysive Pharmaceuticals, USA); SC-236, (Pfizer, USA); ABT-567, (Abbott, USA); Metastatin, (EntreMed, USA); angiogenesis inhibitor, (Tripep, Sweden); maspin, (Sosei, Japan); 2-methoxyestradiol, (Oncology Sciences Corporation, USA); ER-68203-00, (IVAX, USA); Benefin, (Lane Labs, USA); Tz-93, (Tsumura, Japan); TAN-1120, (Takeda, Japan); FR-111142, (Fujisawa, Japan, JP 02233610); platelet factor 4, (RepliGen, USA, EP 407122); vascular endothelial growth factor antagonist, (Borean, Denmark); cancer therapy, (University of South Carolina, USA); bevacizumab (pINN), (Genentech, USA); angiogenesis inhibitors, (SUGEN, USA); XL 784, (Exelixis, USA); XL 647, (Exelixis, USA); MAb, alpha5beta3 integrin, second generation, (Applied Molecular Evolution, USA and MedImmune, USA); gene therapy, retinopathy, (Oxford BioMedica, UK); enzastaurin hydrochloride (USAN), (Lilly, USA); CEP 7055, (Cephalon, USA and Sanofi-Synthelabo, France); BC 1, (Genoa Institute of Cancer Research, Italy); angiogenesis inhibitor, (Alchemia, Australia); VEGF antagonist, (Regeneron, USA); rBPI 21 and BPI-derived antiangiogenic, (XOMA, USA); PI 88, (Progen, Australia); cilengitide (pINN), (Merck KGaA, German; Munich Technical University, Germany, Scripps Clinic and Research Foundation, USA); cetuximab (INN), (Aventis, France); AVE 8062, (Ajinomoto, Japan); AS 1404, (Cancer Research Laboratory, New Zealand); SG 292, (Telios, USA); Endostatin, (Boston Childrens Hospital, USA); ATN 161, (Attenuon, USA); ANGIOSTATIN, (Boston Childrens Hospital, USA); 2-methoxyestradiol, (Boston Childrens Hospital, USA); ZD 6474, (AstraZeneca, UK); ZD 6126, (Angiogene Pharmaceuticals, UK); PPI 2458, (Praecis, USA); AZD 9935, (AstraZeneca, UK); AZD 2171, (AstraZeneca, UK); vatalanib (pINN), (Novartis, Switzerland and Schering AG, Germany); tissue factor pathway inhibitors, (EntreMed, USA); pegaptanib (Pinn), (Gilead Sciences, USA); xanthorrhizol, (Yonsei University, South Korea); vaccine, gene-based, VEGF-2, (Scripps Clinic and Research Foundation, USA); SPV5.2, (Supratek, Canada); SDX 103, (University of California at San Diego, USA); PX 478, (ProIX, USA); METASTATIN, (EntreMed, USA); troponin I, (Harvard University, USA); SU 6668, (SUGEN, USA); OXI 4503, (OXiGENE, USA); o-guanidines, (Dimensional Pharmaceuticals, USA); motuporamine C, (British Columbia University, Canada); CDP 791, (Celltech Group, UK); atiprimod (pINN), (GlaxoSmithKline, UK); E 7820, (Eisai, Japan); CYC 381, (Harvard University, USA); AE 941, (Aeterna, Canada); vaccine, angiogenesis, (EntreMed, USA); urokinase plasminogen activator inhibitor, (Dendreon, USA); oglufanide (pINN), (Melmotte, USA); HIF-1alfa inhibitors, (Xenova, UK); CEP 5214, (Cephalon, USA); BAY RES 2622, (Bayer, Germany); Angiocidin, (InKine, USA); A6, (Angstrom, USA); KR 31372, (Korea Research Institute of Chemical Technology, South Korea); GW 2286, (GlaxoSmithKline, UK); EHT 0101, (ExonHit, France); CP 868596, (Pfizer, USA); CP 564959, (OSI, USA); CP 547632, (Pfizer, USA); 786034, (GlaxoSmithKline, UK); KRN 633, (Kirin Brewery, Japan); drug delivery system, intraocular, 2-methoxyestradiol, (EntreMed, USA); anginex, (Maastricht University, Netherlands, and Minnesota University, USA); ABT 510, (Abbott, USA); AAL 993, (Novartis, Switzerland); VEGI, (ProteomTech, USA); tumor necrosis factor-alpha inhibitors, (National Institute on Aging, USA); SU 11248, (Pfizer, USA and SUGEN USA); ABT 518, (Abbott, USA); YH16, (Yantai Rongchang, China); S-3APG, (Boston Childrens Hospital, USA and EntreMed, USA); MAb, KDR, (ImClone Systems, USA); MAb, alpha5 beta1, (Protein Design, USA); KDR kinase inhibitor, (Celltech Group, UK, and Johnson & Johnson, USA); GFB 116, (South Florida University, USA and Yale University, USA); CS 706, (Sankyo, Japan); combretastatin A4 prodrug, (Arizona State University, USA); chondroitinase AC, (IBEX, Canada); BAY RES 2690, (Bayer, Germany); AGM 1470, (Harvard University, USA, Takeda, Japan, and TAP, USA); AG 13925, (Agouron, USA); Tetrathiomolybdate, (University of Michigan, USA); GCS 100, (Wayne State University, USA) CV 247, (Ivy Medical, UK); CKD 732, (Chong Kun Dang, South Korea); MAb, vascular endothelium growth factor, (Xenova, UK); irsogladine (INN), (Nippon Shinyaku, Japan); RG 13577, (Aventis, France); WX 360, (Wilex, Germany); squalamine (pINN), (Genaera, USA); RPI 4610, (Sirna, USA); cancer therapy, (Marinova, Australia); heparanase inhibitors, (InSight, Israel); KL 3106, (Kolon, South Korea); Honokiol, (Emory University, USA); ZK CDK, (Schering AG, Germany); ZK Angio, (Schering AG, Germany); ZK 229561, (Novartis, Switzerland, and Schering AG, Germany); XMP 300, (XOMA, USA); VGA 1102, (Taisho, Japan); VEGF receptor modulators, (Pharmacopeia, USA); VE-cadherin-2 antagonists, (ImClone Systems, USA); Vasostatin, (National Institutes of Health, USA); vaccine, Flk-1, (ImClone Systems, USA); TZ 93, (Tsumura, Japan); TumStatin, (Beth Israel Hospital, USA); truncated soluble FLT 1 (vascular endothelial growth factor receptor 1), (Merck & Co, USA); Tie-2 ligands, (Regeneron, USA); and, thrombospondin 1 inhibitor, (Allegheny Health, Education and Research Foundation, USA).

Alternatively, the present compounds may also be used in co-therapies with other anti-neoplastic agents, such as VEGF antagonists, other kinase inhibitors including p38 inhibitors, KDR inhibitors, EGF inhibitors (such as panitumumab), CDK inhibitors, TNF inhibitors, metallomatrix proteases inhibitors (MMP), COX-2 inhibitors including celecoxib, NSAID's, $\alpha_v\beta_3$ inhibitors, phosphatidylinitisol 3-kinase inhibitors, AKT/PCK inhibitors, proteasome inhibitors (such as Velcade™), Trail receptor agonists (such as AMG 655), Trail (such as AMG 951), XIAP inhibitors, BC12 inhibitors, Aurora kinase inhibitors, Raf kinases inhibitors, ubiquitin ligase inhibitors, HGF inhibitors (such as AMG 102), and c-Met inhibitors (such as compounds described WO 06/116713 and U.S. Ser. No. 11/879,034).

Also included in the family of compounds of the current are the pharmaceutically acceptable salts and solvates thereof. The term "pharmaceutically-acceptable salts" embraces salts commonly used to form alkali metal salts and to form addition salts of free acids or free bases. The nature of the salt is not critical, provided that it is pharmaceutically acceptable. Suitable pharmaceutically acceptable acid addition salts of compounds of the current invention may be prepared from an inorganic acid or from an organic acid. Examples of such inorganic acids are hydrochloric, hydrobromic, hydroiodic, nitric, carbonic, sulfuric and phosphoric acid. Appropriate organic acids may be selected from aliphatic, cycloaliphatic, aromatic, arylaliphatic, heterocyclic, carboxylic and sulfonic classes of organic acids, example of which are formic, acetic, adipic, butyric, propionic, succinic, glycolic, gluconic, lactic, malic, tartaric, citric, ascorbic, glucuronic, maleic, fumaric, pyruvic, aspartic, glutamic, benzoic, anthranilic, mesylic, 4-hydroxybenzoic, phenylacetic, mandelic, embonic (pamoic), methanesulfonic, ethanesulfonic, ethanedisulfonic, benzenesulfonic, pantothenic, 2-hydroxyethanesulfonic, toluenesulfonic, sulfanilic, cyclohexylaminosulfonic, camphoric, camphorsulfonic, digluconic, cyclopentanepropionic, dodecylsulfonic, glucoheptanoic, glycerophosphonic, heptanoic, hexanoic, 2-hydroxy-ethanesulfonic, nicotinic, 2-naphthalenesulfonic, oxalic, palmoic, pectinic, persulfuric, 2-phenylpropionic, picric, pivalic propionic, succinic, tartaric, thiocyanic, mesylic, undecanoic, stearic, algenic, β-hydroxybutyric, salicylic, galactaric and galacturonic acid. Suitable pharmaceutically-acceptable base addition salts of compounds of the current invention include metallic salts, such as salts made from aluminum, calcium, lithium, magnesium, potassium, sodium and zinc, or salts made from organic bases including primary, secondary and tertiary amines, substituted amines including cyclic amines, such as caffeine, arginine, diethylamine, N-ethyl piperidine, aistidine, glucamine, isopropylamine, lysine, morpholine, N-ethyl morpholine, piperazine, piperidine, triethylamine, trimethylamine. All of these salts may be prepared by conventional means from the corresponding compound of the invention by reacting, for example, the appropriate acid or base with the compound of the current invention. When a basic group and an acid group are present in the same molecule, a compound of the current invention may also form internal salts.

GENERAL SYNTHETIC PROCEDURES

The compounds of the invention can be synthesized according to the following procedures.

The following abbreviations are used throughout the specification:

| | |
|---|---|
| BH$_3$ | borane |
| EtOAc | ethyl acetate |
| HCl | hydrochloric acid |
| KOt-Bu | potassium butoxide |
| MeOH, CH$_3$OH | methanol |
| NMP | N-methylpyrrolidinone, or (1-Methyl-2-pyrrolidinone) |
| K$_2$CO$_3$ | potassium carbonate |
| Tol | toluene |

Example 1

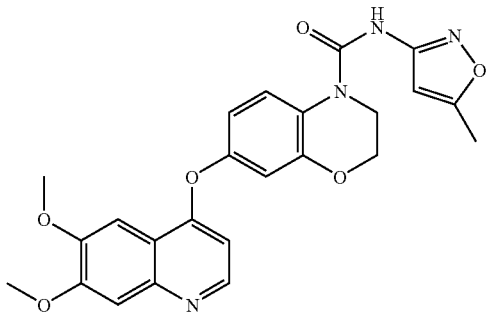

7-((6,7-bis(methyloxy)-4-quinolinyl)oxy)-N-(5-methyl-3-isoxazolyl)-2,3-dihydro-4H-1,4-benzoxazine-4-carboxamide The title compound was synthesized as described below.

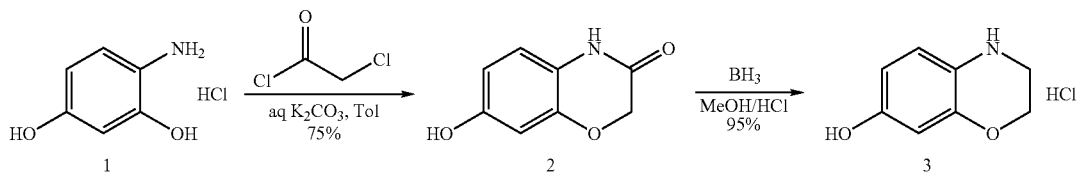

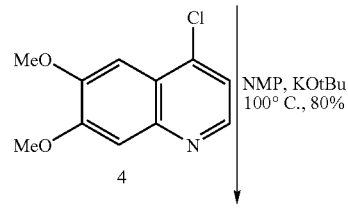

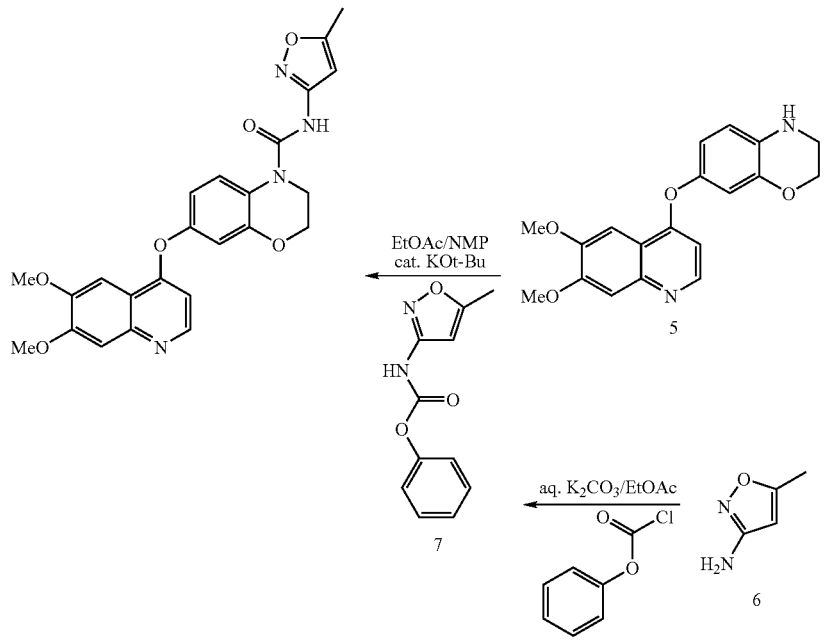

7-Hydroxy-2H-benzo[b][1,4]oxazin-3(4H)-one (2)

$K_2CO_3$ (250 g, 1.8 mol, 4 eq) was dissolved in water (1100 mL) in a 3 L round bottomed flask, vacuum degassed 3 times, then cooled to 0 to 5° C. 4-Amino resorcinol HCl (73 g, 0.45 mol, 1 eq) was added though a strong nitrogen purge, and the blue solution was again degassed 3×. Choroacetyl chloride (45 mL, 64 g, 0.57 mol, 1.25 eq) was dissolved in toluene (225 mL), and was added over 1 h maintaining the temperature below 5° C. the ice bath was removed, and the mixture (biphasic with suspended crystalline product) was stirred overnight. The intermediate 2 was then isolated via filtration giving 53 g (71%) after a water wash (550 mL) and drying.

3,4-Dihydro-2H-benzo[b][1,4]oxazin-7-ol Hydrochloride (3)

To a 2 L round bottomed flask was charged with 7-hydroxy-2H-benzo[b][1,4]oxazin-3(4H)-one 2 (30.5 g, 185 mmol) and anhydrous THF (90 mL) under $N_2$. The suspension was cooled to 5° C., and borane-THF complex (1 M in THF, 480 ml, 480 mmol, 2.6 equiv) was added over 40 min under a stream of $N_2$ to remove the $H_2$ generated. Upon complete addition (T=15° C.), the now colorless solution was removed from the ice bath and allowed to warm to ambient temperature. After stirring overnight, an aliquot was quenched into MeOH and analyzed by HPLC.

The solution was quenched by the slow addition (1 h) of MeOH (80 mL) under a stream of $N_2$. The mixture was then stirred at ambient temperature for 6 h to allow for complete destruction of the borate complex to product and trimethyl borane.

The resulting solution was concentrated by rotary evaporation, flushed with methanol, and the pale yellow residue was dissolved in MeOH (80 mL). The solution was then cooled in an ice bath under $N_2$ and a solution of HCl (1 M in $Et_2O$, 200 mL, 200 mmol, 1.08 eq) was added over 10 min, giving the product as a white crystalline solid suspended in a bright blue solution. MTBE (120 mL) was added over 30 min, and the mixture was allowed to age overnight at ambient temperature. The pale blue solid was filtered and washed nearly white with MTBE/MeOH (4:1, 100 mL), then was dried under vacuum overnight to yield 32.7 g, (95%) 3,4-dihydro-2H-benzo[b][1,4]oxazin-7-ol hydrochloride (3).

7-(6,7-dimethoxyquinolin-4-yloxy)-3,4-dihydro-2H-benzo[b][1,4]oxazine (5)

1-Methyl-2-pyrrolidinone (NMP), anhydrous 99.5% (12.6 L) was charged into a 100 L reactor at ambient temperature followed by 3,4-dihydro-2H-benzo[b][1,4]oxazin-7-ol hydrochloride 3 (1.5779 Kg, 8.41 mol, 1.5 equiv.) and 4-chloro-6,7-dimethoxyquinoline 4 (1.2539 Kg, 5.61 mol, 1.0 equiv.) A 1.6 L portion of NMP was used to rinse the reactor walls. Reactor contents were cooled to 10° C. A series of 3 vacuum purges were performed on the reactor. A charge of potassium tert-butoxide, min 94.0% (1.9235 Kg, 17 mol, 3.0 equiv.) was delivered into the reactor in 3 portions.

A final 1.7 L portion of NMP was added as rinse. Reactor was purged with vacuum/$N_2$ cycles 3 more times. Reactor contents were heated to 100° C. and subsequently held for 18 hours at an agitation rate of 118 rpm. Completion was marked when 4-chloro-6,7-dimethoxyquinoline was <0.5% area at 220 nm after 18 hours. The reactor contents were cooled to 25° C. and the reaction mixture was seeded with 5.0 g of GMP penultimate, followed by purified water addition of 9.3 L over a 10 minute period. The internal temperature rose by 30° C. The mixture was cooled to ambient and the remaining 22.5 L of purified water was charged in slowly. The reactor contents were held for 1 hour at 25° C. with stir rate of 199 rpm. The thick off-white slurry was then transferred from the reactor through the centrifuge and into the receiver. Filtration was followed by the recirculation of filtrate over the wet cake to minimize the product loss. In addition, one NMP:water wash (2:1 ratio 10.5 L water:5.25 L NMP) and one water wash of 15.8 L was performed. Rotation speed on the centrifuge was 230 rpm for the filtration and water/NMP rinse. It was increased to 444 rpm for the water wash and was let to spin out at 512 rpm for 2 hours.

Recrystallization of 5

A 100 L reactor was charged with 14.7 L of purified water and set to 20° C. The wet cake was transferred from the centrifuge in to the reactor followed by 1-methyl-2-pyrrolidinone (NMP), anhydrous, 99.5% (7.35 L). The contents of the reactor were agitated at 135 rpm over 17 hours. The thick off-white slurry was then transferred from the reactor through the centrifuge and into the receiver. Filtration was followed by the recirculation of filtrate over the wet cake to minimize the product loss. Reactor was rinsed and wet cake was washed with 45 L of purified water in portions. Rotation speed on the centrifuge was 230 rpm for the filtration, 340 rpm for recirculation, 418 rpm for the first 15 L of water wash and 513 rpm for the rest of the water wash and spin out. Product was held spinning in the centrifuge under nitrogen for 17 hours. Subsequently, the batch was dried at 35° C. in vacuum oven with high N2 flow for 7 days. The process yielded 1.4008 Kg (73%) of 7-(6,7-dimethoxyquinolin-4-yloxy)-3,4-dihydro-2H-benzo[b][1,4]oxazine. 5

Phenyl 5-methylisoxazol-3-ylcarbamate (7)

Purified water, USP (9.5 L) was charged into a 100 L reactor at 20° C. followed by potassium carbonate, (powder 325 mesh, 98+%, 3.3183 Kg, 24 mol, 2.5 equiv.); 3-amino-5-methylisoxazole (942 g, 9.6 mol, 1.0 equiv.), and ethyl acetate (28.25 L, 30 volumes). Additional 250 mL of water was used to rinse the walls of the reactor. Contents of the reactor were cooled to 5° C. and 2 vacuum purges were performed. Phenyl chloroformate, 99%, (2.974 Kg, 19 mol, 2.0 equiv.) was charged slowly while maintaining the internal temperature $\leq$30° C. At the end of addition the reactor temperature was set to 20° C. with agitation rate of 148 rpm. Reactor contents were held for 90 minutes at 20° C. resulting in a triphasic mixture with solid (product) in the mid layer. The reactor temperature was increased to 35° C. in order to dissolve the solids and obtain a biphasic mixture more suitable for sampling. Completion was marked when 3-amino-5-methylisoxazole was <0.5% area at 220 nm. The agitation was stopped and the layers were allowed to separate at 35° C. The aqueous layer was drained and a 10% sodium carbonate solution (4.15 L) was charged and agitation resumed at 35° C. After 30 minutes the agitation was stopped. The layers were separated and aqueous layer was drained. The organic layer was treated with 2 more purified water washes (6.5 L each) at 35° C. Following the last separation the organic layer was set for distillation with a jacket temperature of 85° C. The distillation was performed under a slight vacuum (12 psi) and a total of 18 L of EtOAc was collected.

The contents of the reactor were cooled to 0° C. at ramp rate of 1.6° C./min and held at 0° C. for 2 hours. The thick white suspension was then transferred from the reactor through the Aurora filter and in to the receiver. Filtration was followed by the recirculation of filtrate over the wet cake and one cold EtOAc wash (2.0 L). The product was held on the filter under nitrogen for 3 hours prior to the transfer to vacuum oven. The material was dried at 35° C. over 2 days with strong nitrogen purge yielding 1.5450 Kg (74.3% yield) of 100% analytically pure product. A physical loss in the reactor of 96.23 g, (4.6%) of 99.8% analytically pure carbamate was later observed. The loss in the ML was 375.8 g, (18%) and in wash was 78.7 g, (3.8%).

Title Compound

To a 100 L vessel was charged NMP (anhydrous, 1900 mL), 5 (1378 g, 4.07 mol, 100 mol %) and ethyl acetate (12.5 L). The vessel was purged with nitrogen, agitation set at 276 rpm, and then the suspension was heated to 60° C. The solids dissolved, and the solution was passed though a 5 micron in-line filter (polypropylene) into a separate 100 L vessel. The filter was rinsed with a 57° C. mixture of NMP (185 mL) and EtOAc (1200 mL) prepared in the initial vessel.

To the initial vessel was charged NMP (1100 mL), 7 (1345 g, 6.16 mol, 151 mol %) and EtOAc (7100 L). The mixture was heated as above to 60° C. to achieve dissolution, and was passed thought the same filter to the second vessel. A 60° C. wash consisting of NMP (185 mL) and EtOAc (1200 mL) was passed though the filter.

To the second vessel was charged potassium t-butoxide (1.1 g), the vessel was vacuum purged, and the reaction was heated to 65° C. Within ½ h, crystals had formed in the reaction. After a 3 h age, the reaction was assayed, and was deemed complete with 0.8 LCAP penultimate remaining.

The mixture was cooled to 25° C., and was aged overnight. The solid product was collected by filtration in an Aurora filter (5 micron polypropylene filter-cloth), and any remaining product left in the vessel was collected by liquor recycle. The product was washed with EtOAc (4×2700 mL), and then was dried via nitrogen purge through the Aurora for 3 days.

A total of 1.7146 Kg (92%) of title compound was isolated as a light brown solid. $^1$H NMR (400 MHz, DMSO-d$_6$) d ppm 10.16 (s, 1 H), 8.49 (d, J=5.31 Hz, 1 H), 7.70 (d, J=8.84 Hz, 1 H), 7.48 (s, 1 H), 7.39 (s, 1 H), 6.81-6.83 (m, 1 H), 6.76-6.80 (m, 1 H), 6.55 (d, J=5.18 Hz, 1 H), 6.51-6.53 (m, 1 H), 4.27-4.31 (m, 2 H), 3.94 (s, 3 H), 3.93 (s, 3 H), 3.88-3.91 (m, 2 H), 2.37 (s, 3 H). HRMS (M+H)$^+$ calc'd: 463.1612 found: 463.1634.

Example 2

Compound A free base is known to exist in at least three anhydrous crystalline forms as well as a methanol solvate. All four forms have a unique powder X-ray powder diffraction (XRPD) patterns, the major peaks of which are shown below:

| FORM | Powder X-ray Diffraction Peaks (Approximate °2 Theta) |
|---|---|
| Form I | 4.5, 9.5, 16.0, 24.0 |
| Form II | 5.6, 8.8, 11.2, 13.6, 14.9, 24.8 |
| Form III | 10.3, 13.5, 14.3, 16.4, 19.6 |
| Methanol Solvate | 5.7, 8.9, 9.3, 11.3, 11.9, 13.1, 18.4, 24.8, 26.7 |

With heating at 10° C./minute, anhydrous Form I converts to anhydrous Form II at a temperature of ~150° C., and Form II decomposes near 240° C. Form III decomposes near 235° C. The methanol solvate liberates methanol near 135° C. and converts to anhydrous Form II.

Compound A has also been shown to form crystalline salts with methanesulfonic acid, phosphoric acid, sulfuric acid and hydrochloric acid. The mesylate salt is known to exist in at least two crystalline forms with unique X-ray powder diffraction patterns, the major peaks of which are shown below:

| FORM | Powder X-ray Diffraction Peaks (Approximate °2 Theta) |
| --- | --- |
| Form I | 6.7, 10.2, 12.0, 14.9, 17.8 |
| Form II | 4.2, 4.9, 9.9, 22.1, 25.6 |

Form I mesylate salt has been formed by suspending the free base in EtOH, adding a slight molar excess of methanesulfonic acid, heating to dissolve and slowly cooling to room temperature. The resulting solid was then isolated by filtration. Form II mesylate salt has been formed by suspending the free base in isopropyl alcohol (IPA), adding a slight molar excess of methanesulfonic acid, heating to dissolve and slowly cooling to room temperature. The resulting solid was then isolated by filtration.

The hydrochloride salt is formed by preparing a solution of Compound A free base in ethanol and adding hydrochloric acid in slight molar excess with stirring and optional heat. Spontaneous salt formation occurred both with and without the application of heating and cooling. The hydrochloride salt is known to exist in at least one anhydrous form, which has been confirmed by single-crystal X-ray analysis, and at least one hydrous form. The anhydrous form of the hydrochloride salt is crystalline and decomposes near 230° C. when heated at a rate of 10° C./minute. The hydrous form of Compound A hydrochloride has been obtained by suspending the anhydrous hydrochloride material in water or in dilute aqueous solutions of hydrochloric acid. The hydrous material is crystalline, can freely absorb up to 4 molar equivalents of water at 90% relative humidity and 25° C., and appears to fully dehydrate by 150° C. and decompose near 170° C. when heated at a rate of 10° C./minute. Both the anhydrous and hydrous forms of Compound A hydrochloride have unique X-ray powder diffraction patterns, the major peaks of which are described below:

| FORM | Powder X-ray Diffraction Peaks (Approximate °2 Theta) |
| --- | --- |
| Anhydrous | 5.2, 10.5, 12.0, 15.5, 17.3, 19.7, 24.2 |
| Hydrous | 8.4, 9.5, 11.2, 12.3, 16.9, 24.5 |

Apparent phosphoric acid salt material was generated by high throughput screening out of one or more of the following: Acetone:Water (1:1), Tetrahydrofuran (THF), THF:Water (9:1), methyl ethyl ketone (MEK), isopropyl acetate (IPAc), toluene, ethanol, ethanol:water (9:1), isopropyl alcohol (IPA), IPA:water (9:1) and acetonitrile. Samples were initially prepared by: 1) adding free base to the crystallization source plate, 2) adding a slight molar excess of acid, 3) adding the crystallization solvent to a final concentration of ~16 mg/mL, and 4) heating to 55° C. for 1 hour with stirring. The samples were then filtered and split for crystallization by evaporation, cooling or anti-solvent addition with n-butyl ether. The crystallization plates were centrifuged, and the supernatants were aspirated allowing for microscopic and XRPD analyses of any resulting solids. Any solid remaining in the source plate was also analyzed by microscopy and XRPD. The experiments with phosphoric acid resulted in two possible crystalline salts.

Apparent sulfuric acid salt material was generated by high throughput screening as described above. The experiments with sulfuric acid resulted in two possible crystalline salts.

Apparent hydrochloric acid salt material was generated by high throughput screening as described above. The high throughput experiments with hydrochloric acid resulted in two possible crystalline salts.

Apparent methanesulfonic acid salt material was generated by high throughput screening as described above. The high throughput experiments with methanesulfonic acid resulted in three possible crystalline salts.

Of course, it will be understood that salts can be generated using different organic solvents than those described above. It is believed that other acid addition salts of Compound A are possible with counter-ions from organic and inorganic acids, preferably those having pKa <5. It is also understood that additional physical forms of free base and various salts may exist.

Example 3

In Vitro Metabolite Profiling

Incubation mixtures were prepared including [14C]-Compound A (10 µM, 0.5 µCi), liver microsomes at 1 mg/mL (human, mouse, rat, monkey, rabbit, dog), $MgCl_2$ (3 mM), and potassium phosphate buffer (100 mM). The reaction was started by adding NADPH (1 mM) and incubations were carried out in a shaking water bath maintained at 37° C. for 1 hr. The reactions were stopped by adding 1 volume of ACN:MeOH 1:1 mixture; vortex mixed; centrifuged at 16000×g. The supernatants were analyzed on a reverse phase HPLC (Agilent 1100, Agilent systems, DE) in line with a radiomatic (β-ram, IN/US systems, FL) detector and an LTQ ion-trap mass spectrometer (ThermoFisher, San Jose, Calif.). HPLC separations were carried out on a phenyl-hexyl luna (150×4.6 mm, 5 µm, Phenomenex Inc) column maintained at 40° C. at a flow rate of 1 mL/min. A binary mobile phase consisting of 10 mM ammonium formate in $H_2O$ (solvent A) and 0.1% formic in MeOH (solvent B) was employed under the following gradient conditions: 0 to 2 min, 95% A; 2 to 10 min, 95 to 75% A; 10 to 40 min, 75 to 60% A; 40 to 60 min, 60 to 55% A; 60 to 77 min, 55 to 25% A; 77 to 78 min, 25 to 5% A; 78 to 83 min, 5% A; 83 to 84 min, 5 to 95% A; 84 to 90 min, 95% A. The flow post-column was split such that 80% went to radiomatic detector and the remaining 20% to MS. The flow into radiomatic detector was mixed with 3 volumes of liquid scintillant (UltimaFlow, PerkinElmer) prior to radio-detection.

Substantial turnover of Compound A was observed in all species. The following compounds identified in Table 16 below were the significant metabolites formed in all species. These same metabolites were also formed upon incubating Compound A with recombinant human cytochrome P450 3A4 isomform fortified with NADPH.

TABLE 16

| Metabolite | KDR Inhibition (μM) | Retention Time (min) | NMR |
|---|---|---|---|
| (structure: 6,7-dimethoxyquinoline N-oxide linked via O to 2,3-dihydrobenzo[1,4]oxazine-4-carboxamide N-(5-methylisoxazol-3-yl)) | 5 | 75 | 1H NMR (400 MHz, DMSO-d$_6$) ppm 10.15 (s, 1H), 8.31 (d, J = 6.82 Hz, 1H), 7.93 (s, 1H), 7.68 (d, J = 8.84 Hz, 1H), 7.47 (s, 1H), 6.74-6.86 (m, 2H), 6.58 (d, J = 6.95 Hz, 1H), 6.52 (s, 1H), 4.25-4.31 (m, 2H), 3.99 (s, 3H), 3.95 (s, 3H), 3.85-3.91 (m, 2H), 2.37 (s, 3H). |
| (structure: 7-hydroxy-6-methoxyquinoline linked via O to 2,3-dihydrobenzo[1,4]oxazine-4-carboxamide N-(5-methylisoxazol-3-yl)) | 0.777202 | 59.5 | 1H NMR (400 MHz, DMSO-d$_6$) ppm 10.16 (s, 1H), 10.10 (s, 1H), 8.42 (d, J = 5.2 Hz, 1H), 7.69 (d, J = 9.0 Hz, 1H), 7.45 (s, 1H), 7.27 (s, 1H), 6.73-6.83 (m, 2H), 6.52 (s, 1H), 6.47 (d, J = 5.3 Hz, 1H), 4.24-4.32 (m, 2H), 3.93 (s, 3H), 3.84-3.92 (m, 2H), 2.37 (s, 3H) |
| (structure: 6-hydroxy-7-methoxyquinoline linked via O to 2,3-dihydrobenzo[1,4]oxazine-4-carboxamide N-(5-methylisoxazol-3-yl)) | 0.001684 | 55.1 | 1H NMR (400 MHz, DMSO-d$_6$) ppm 10.06 (s, 2H), 8.44 (d, J = 5.2 Hz, 1H), 7.67 (d, J = 8.8 Hz, 1H), 7.42 (s, 1H), 7.36 (s, 1H), 6.68-6.80 (m, 2H), 6.48-6.57 (m, 2H), 4.23-4.33 (m, 2H), 3.94 (s, 3H), 3.83-3.91 (m, 2H), 2.37 (s, 3H) |

TABLE 16-continued

| Metabolite | KDR Inhibition (μM) | Retention Time (min) | NMR |
|---|---|---|---|
| 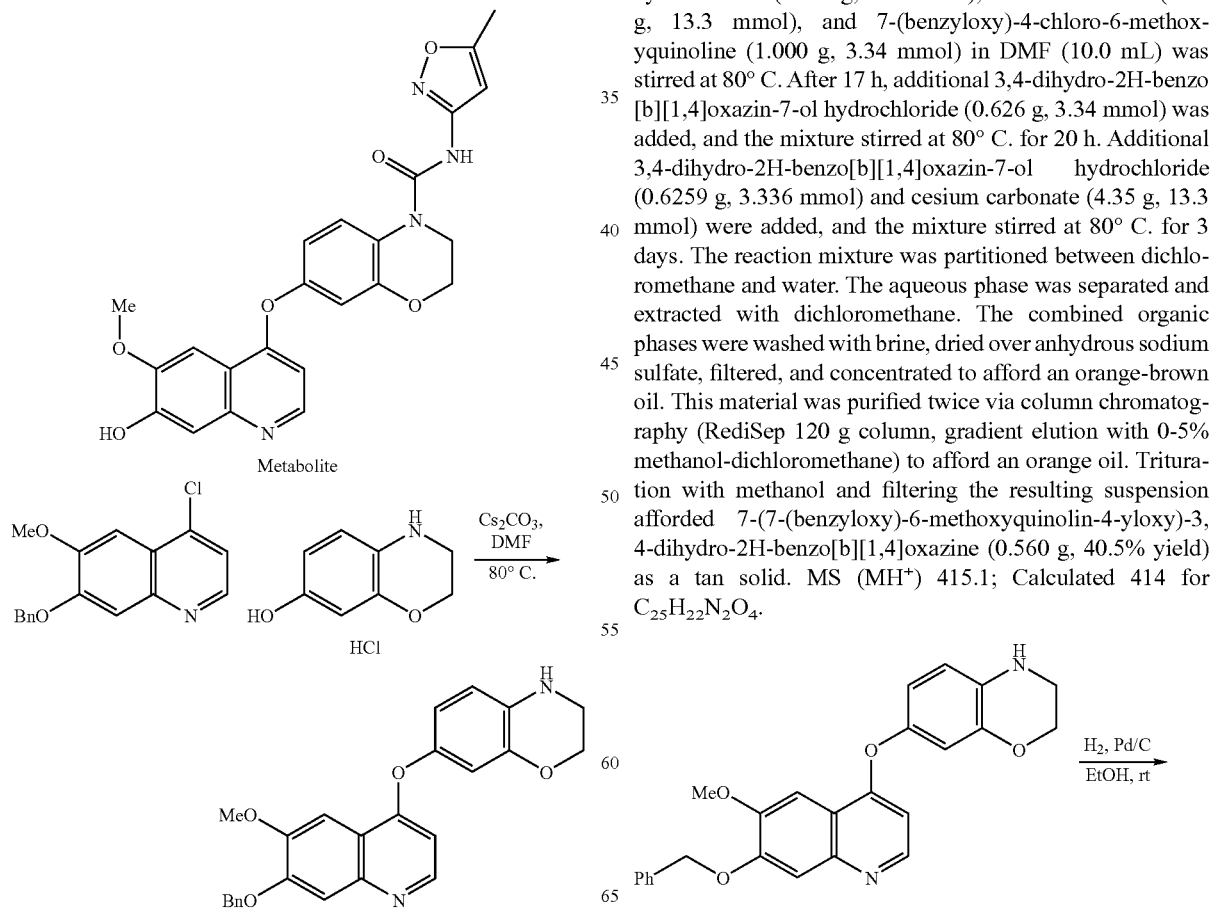 | 0.001042 | 55.1 | 1H NMR (400 MHz, DMSO-d$_6$) ☐ ppm 10.29 (s, 1H), 8.81 (d, J = 6.57 Hz, 1H), 7.81 (d, J = 8.97 Hz, 1H), 7.71 (s, 1H), 7.57 (s, 1H), 6.98-7.02 (m, 1H), 6.89-6.94 (m, 2H), 6.67 (s, 1H), 4.53 (s, 2H), 4.30-4.36 (m, 2H), 3.99-4.06 (m, 6H), 3.89-3.95 (m, 2H). |

Identification of the chemical structure of the metabolites was achieved through comparison with synthesized standards. The Compound A N-oxide standard was synthesized using procedures known in the art. The remaining metabolites was sysnthesized as follows:

7-(7-(benzyloxy)-6-methoxyquinolin-4-yloxy)-3,4-dihydro-2H-benzo[b][1,4]oxazine A solution of 3,4-dihydro-2H-benzo[b][1,4]oxazin-7-ol hydrochloride (0.626 g, 3.34 mmol), cesium carbonate (4.35 g, 13.3 mmol), and 7-(benzyloxy)-4-chloro-6-methoxyquinoline (1.000 g, 3.34 mmol) in DMF (10.0 mL) was stirred at 80° C. After 17 h, additional 3,4-dihydro-2H-benzo[b][1,4]oxazin-7-ol hydrochloride (0.626 g, 3.34 mmol) was added, and the mixture stirred at 80° C. for 20 h. Additional 3,4-dihydro-2H-benzo[b][1,4]oxazin-7-ol hydrochloride (0.6259 g, 3.336 mmol) and cesium carbonate (4.35 g, 13.3 mmol) were added, and the mixture stirred at 80° C. for 3 days. The reaction mixture was partitioned between dichloromethane and water. The aqueous phase was separated and extracted with dichloromethane. The combined organic phases were washed with brine, dried over anhydrous sodium sulfate, filtered, and concentrated to afford an orange-brown oil. This material was purified twice via column chromatography (RediSep 120 g column, gradient elution with 0-5% methanol-dichloromethane) to afford an orange oil. Trituration with methanol and filtering the resulting suspension afforded 7-(7-(benzyloxy)-6-methoxyquinolin-4-yloxy)-3,4-dihydro-2H-benzo[b][1,4]oxazine (0.560 g, 40.5% yield) as a tan solid. MS (MH$^+$) 415.1; Calculated 414 for $C_{25}H_{22}N_2O_4$.

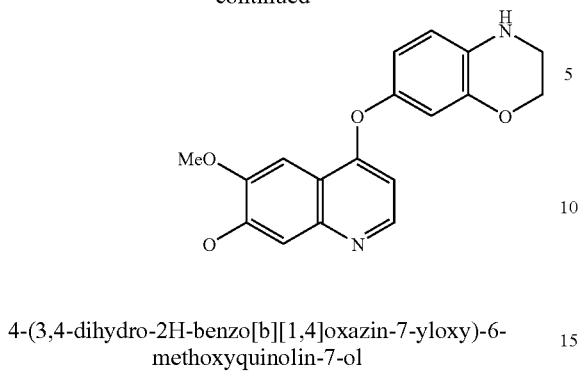

4-(3,4-dihydro-2H-benzo[b][1,4]oxazin-7-yloxy)-6-methoxyquinolin-7-ol

Palladium, 10 wt % on activated carbon (0.050 g, 0.47 mmol) was added to a solution of 7-(7-(benzyloxy)-6-methoxyquinolin-4-yloxy)-3,4-dihydro-2H-benzo[b][1,4]oxazine (0.250 g, 0.60 mmol) in ethanol (10.0 mL). The system was evacuated and purged with hydrogen (g) three times and then stirred under a H$_2$ (g) atmosphere for 20 h. The reaction mixture was filtered through a pad of Celite and concentrated to afford 4-(3,4-dihydro-2H-benzo[b][1,4]oxazin-7-yloxy)-6-methoxyquinolin-7-ol (0.200 g, 102% yield) as a yellow-green solid. MS (MH$^+$) 325.0; Calculated 324 for C$_{18}$H$_{16}$N$_2$O$_4$.

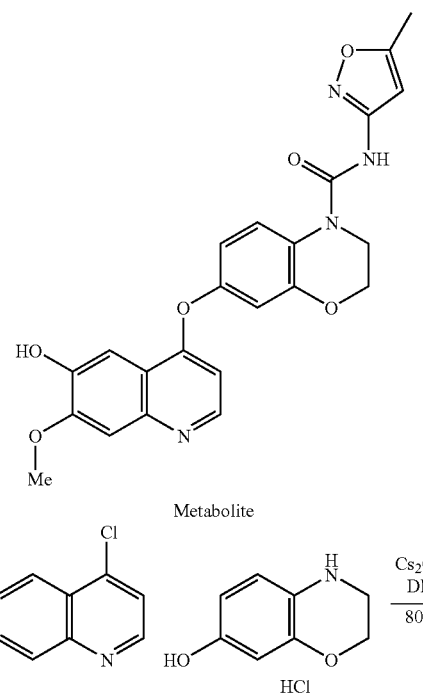

Metabolite

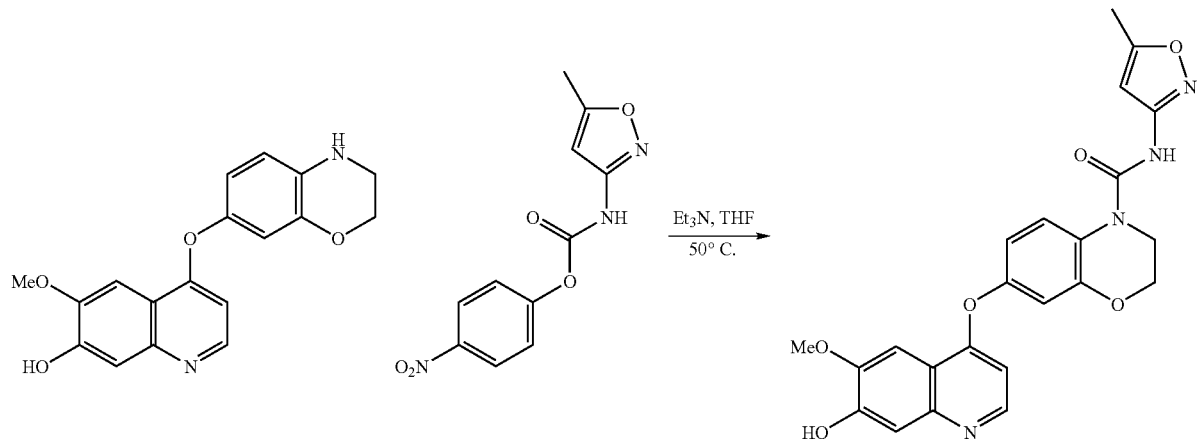

7-(7-hydroxy-6-methoxyquinolin-4-yloxy)-N-(5-methylisoxazol-3-yl)-2,3-dihydrobenzo[b][1,4]oxazine-4-carboxamide A 25-mL round bottomed flask was charged with 4-(3,4-dihydro-2H-benzo[b][1,4]oxazin-7-yloxy)-6-methoxyquinolin-7-ol (0.124 g, 0.38 mmol), 4-nitrophenyl 5-methylisoxazol-3-ylcarbamate (0.11 g, 0.40 mmol), and THF (5.0 mL). Triethylamine (0.160 mL, 1.1 mmol) was added, the system was purged with argon, and the tube was sealed. The mixture stirred at 50° C. for 16 h. The reaction mixture was concentrated and the residue was purified via column chromatography on silica gel (RediSep 40 g column, 100% ethyl acetate for 10 min, followed by 5% methanol/dichloromethane for 20 min) to afford 7-(7-hydroxy-6-methoxyquinolin-4-yloxy)-N-(5-methylisoxazol-3-yl)-2,3-dihydrobenzo[b][1,4]oxazine-4-carboxamide (0.026 g, 15% yield) as a yellow solid.

-continued

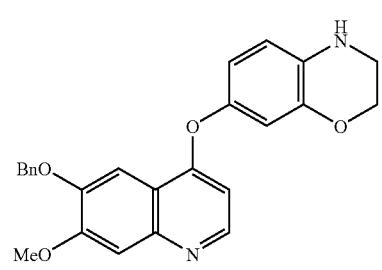

7-(6-(benzyloxy)-7-methoxyquinolin-4-yloxy)-3,4-dihydro-2H-benzo[b][1,4]oxazine A solution of 3,4-dihydro-2H-benzo[b][1,4]oxazin-7-ol hydrochloride (0.626 g, 3.34 mmol), cesium carbonate (4.35 g, 13.3 mmol), and 6-(benzyloxy)-4-chloro-7-methoxyquinoline (1.00 g, 3.34 mmol) in DMF (10.0 mL) was stirred at 80° C. for 18 h. An additional 3,4-dihydro-2H-benzo[b][1,4]oxazin-7-ol hydrochloride (0.626 g, 3.34 mmol) and cesium carbonate (4.35 g, 13.3 mmol) were added, and the mixture stirred at 80° C. for 3 days. The reaction mixture was partitioned between dichloromethane and water. The aqueous phase was separated and extracted with dichloromethane. The combined organic phases were washed with brine, dried over anhydrous sodium sulfate, filtered, and concentrated to afford an orange-brown oil. This material was purified twice via column chromatography (RediSep 80 g column, gradient elution with 0-5% methanol-dichloromethane) to afford an orange oil. Trituration with methanol and filtering the resulting suspension afforded 7-(6-(benzyloxy)-7-methoxyquinolin-4-yloxy)-3,4-dihydro-2H-benzo[b][1,4]oxazine (1.156 g, 83.6% yield) as an orange glass. MS (MH$^+$) 415.1; Calculated 414 for $C_{25}H_{22}N_2O_4$.

4-(3,4-dihydro-2H-benzo[b][1,4]oxazin-7-yloxy)-7-methoxyquinolin-6-ol

Palladium, 10 wt % on activated carbon (0.100 g, 0.940 mmol) was added to a solution of 7-(6-(benzyloxy)-7-methoxyquinolin-4-yloxy)-3,4-dihydro-2H-benzo[b][1,4]oxazine (1.156 g, 2.79 mmol) in ethanol (20.0 mL). The system was evacuated and purged with hydrogen (g) three times and then stirred under a H$_2$ (g) atmosphere for 18 h. Additional palladium, 10 wt % on activated carbon (0.100 g, 0.940 mmol) was added to the reaction mixture. The system was evacuated and purged with hydrogen (g) three times and then stirred under a H$_2$ (g) atmosphere for 20 h. The reaction mixture was filtered through a pad of Celite and concentrated to afford an orange brown solid. This material was purified via column chromatography on silica gel (RediSep 40 g column, gradient elution with 0-100% (90:10:1, dichloromethane/methanol/ammonium hydroxide)-dichloromethane) to afford 4-(3,4-dihydro-2H-benzo[b][1,4]oxazin-7-yloxy)-7-methoxyquinolin-6-ol (0.733 g, 81.0% yield) as a yellow solid. MS (MH$^+$) 325.0; Calculated 324 for $C_{18}H_{16}N_2O_4$.

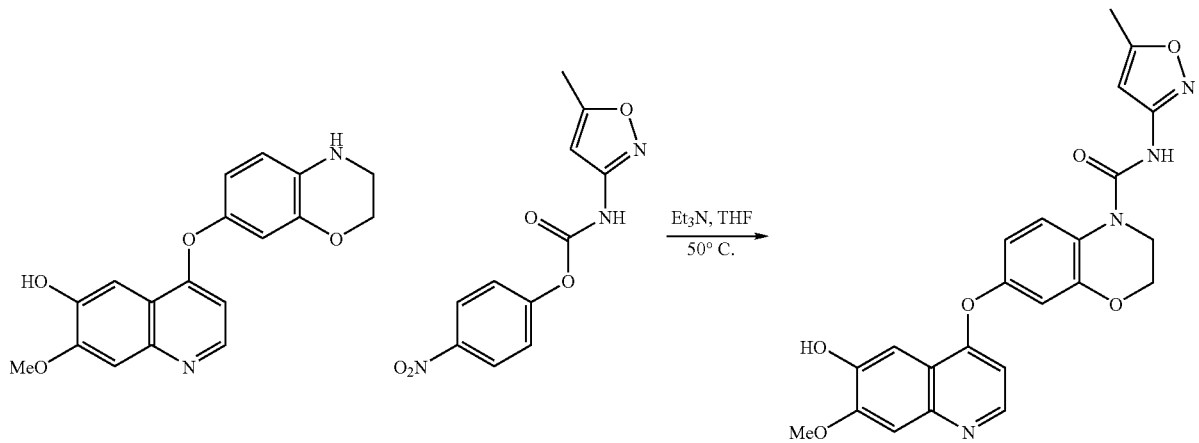

7-(6-hydroxy-7-methoxyquinolin-4-yloxy)-N-(5-methylisoxazol-3-yl)-2,3-dihydrobenzo[b][1,4]oxazine-4-carboxamide A resealable tube was charged with 4-(3,4-dihydro-2H-benzo[b][1,4]oxazin-7-yloxy)-7-methoxyquinolin-6-ol (0.200 g, 0.617 mmol), 4-nitrophenyl 5-methylisoxazol-3-ylcarbamate (0.243 g, 0.925 mmol), and THF (5.0 mL). Triethylamine (0.258 mL, 1.85 mmol) was added, the system was purged with argon, and the tube was sealed. The mixture stirred at 50° C. for 15 h. The reaction mixture was partitioned between ethyl acetate and water. The aqueous phase was separated and extracted with ethyl acetate. The combined organic phases were washed with water and brine, dried over anhydrous sodium sulfate, filtered, and concentrated to afford a yellow-orange oil. This material was purified via column chromatography on silica gel (RediSep 40 g column, eluting with 5% methanol-dichloromethane) to afford a yellow oil. This material was triturated with dichloromethane and filtered to afford 7-(6-hydroxy-7-methoxyquinolin-4-yloxy)-N-(5-methylisoxazol-3-yl)-2,3-dihydrobenzo[b][1,4]oxazine-4-carboxamide (0.104 g, 38% yield) as an off-white solid.

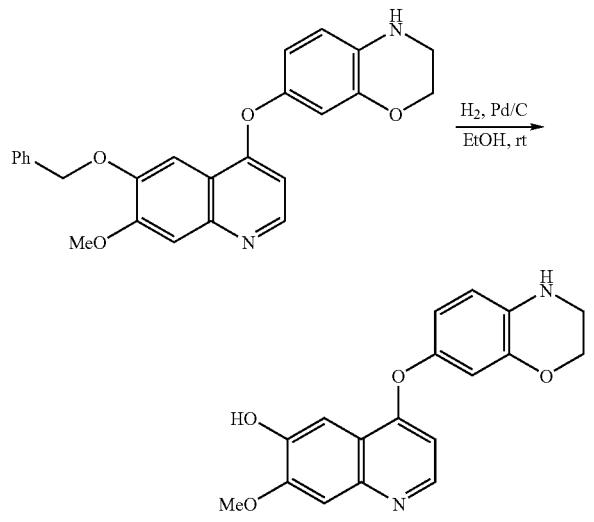

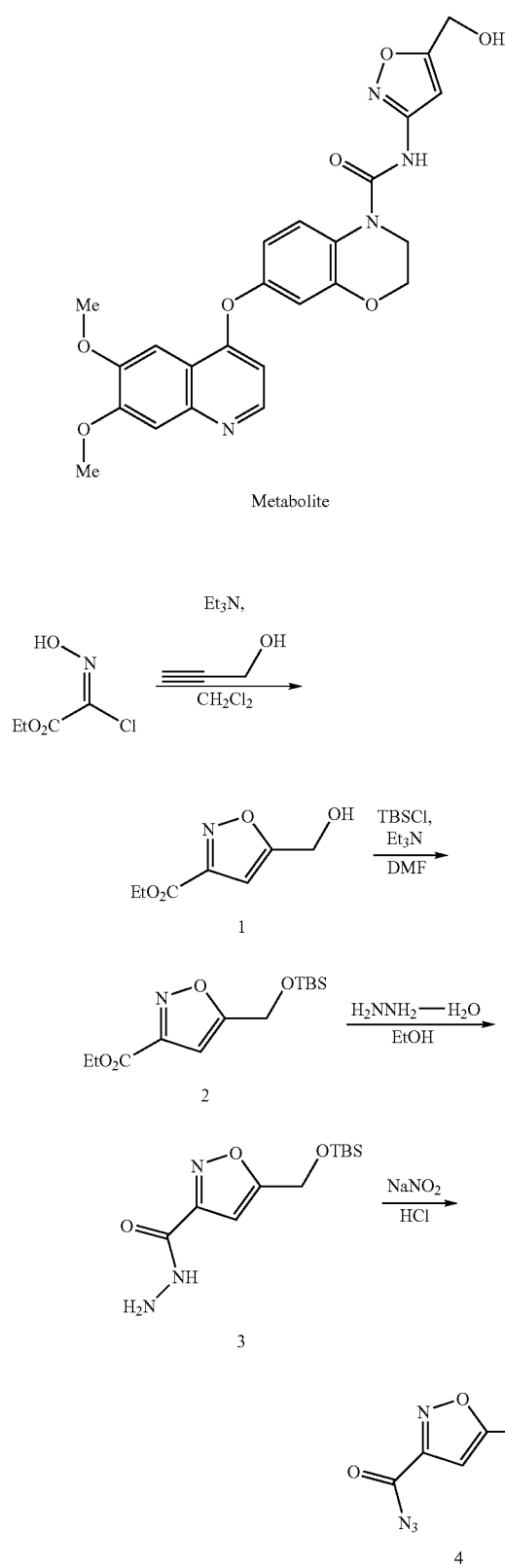

Metabolite

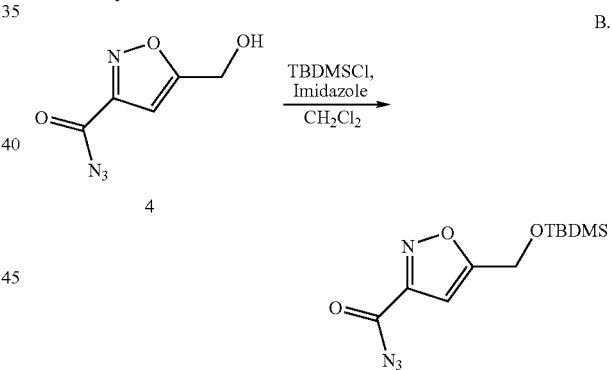

A solution of ethyl chlorooximidoacetate (15 g, 0.1 mol) in CH₂Cl₂ is added dropwise over 4 hours to propargyl alcohol (29 mL, 0.5 mol) and Et₃N (14 mL, 0.1 mmol) in 200 mL CH₂Cl₂. When the addition is complete the reaction mixture is concentrated and triturated with Et₂O. The solid is filtered and the organics are concentrated again. The remaining oil is chromatographed over silica gel (EtOAc/Hex:20/80) to give 5-(hydroxymethyl)isoxazole-3-carboxylate as an oil. The remaining propargyl alcohol is removed by azeotroping from n-heptane.

To a solution of 5-(hydroxymethyl)isoxazole-3-carboxylate (4.0 g, 23 mmol) and TBSCL (3.7 g, 25 mmol) in DMF is added Et₃N (3.4 mL, 24 mmol) dropwise over 20 minutes. The reaction is allowed to stir for 30 minutes after which it is diluted with EtOAc (300 mL), washed with 1 M HCl (3×100 mL), 5% CuSO₄ (2×50 mL) and concentrated in vacuo to yield ethyl-5-({[tert-butyl(dimethylsilyl)]oxy}methyl)isoxazole-3-carboxylate as an oily material.

A mixture of ethyl-5-({[tert-butyl(dimethylsilyl)]oxy}methyl)isoxazole-3-carboxylate (1.68 g, 5.9 mmol) and hydrazine hydrate (44 g, 8.8 mmol) in ethanol (30 mL) is heated to 60° C. for 4 hours. The mixture is cooled to room temperature and the solvents are removed in vacuo to yield 5-({[tert-butyl(dimethyl)silyl]oxy}methyl)isoxazole-3-carbohydrazide as orange crystals.

A mixture of 5-({[tert-butyl(dimethyl)silyl]oxy}methyl)isoxazole-3-carbohydrazide (1.32 g, 4.9 mmol) in concentrated HCl (40 mL) is cooled to 0° C., followed by a dropwise addition of aqueous NaNO₂ (0.42 g, 6.1 mL), maintaining the temperature below 5° C. After 1 hour, the mixture is diluted with water (100 mL) and extracted with EtOAc (3×50 mL). Organics are dried (MgSO₄) and concentrated in vacuo to yield azido(5-(hydroxymethyl)isoxazol-3-yl)methanone (4) as tan crystals.

Azido(5-((tert-butyldimethylsilyloxy)methyl)isoxazol-3-yl)methanone (5)

To a solution of azido(5-(hydroxymethyl)isoxazol-3-yl)methanone (4) (100 mg, 0.60 mmol) and tert-butyldimethylsilylchloride (99 mg, 0.65 mmol) in CH₂Cl₂ (3 mL) at 0° C. was added imidazole (49 mg, 0.71 mmol). After 4 hrs, the mixture was allowed to warm to RT and stirred for an additional 14 hrs. The mixture was cooled to 0° C. and filtered through a short silica gel plug. The plug was rinsed with cold CH₂Cl₂ and the filtrate was concentrated in vacuo to afford crude azido(5-((tert-butyldimethylsilyloxy)methyl)isoxazol-3-yl)methanone (150 mg, 89% yield) as a white solid that was advanced without further purification. MH+=283.1.

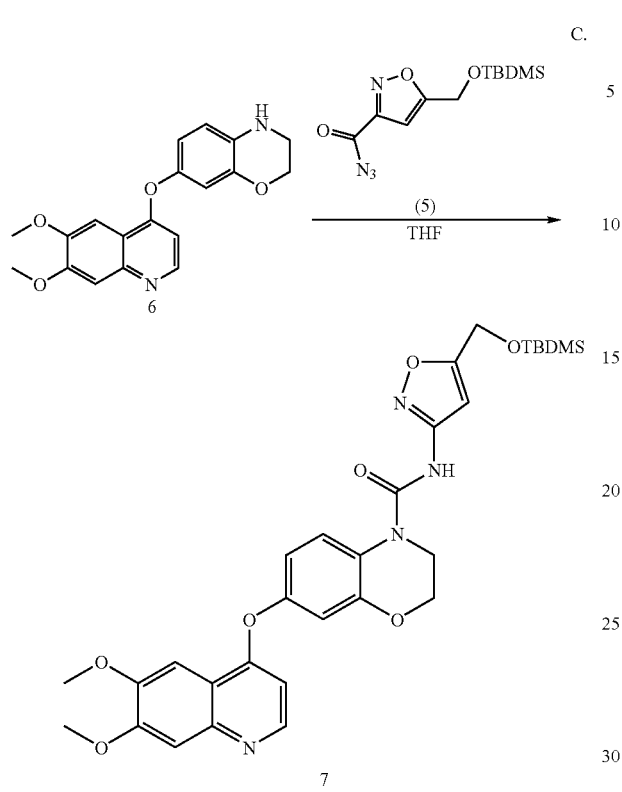

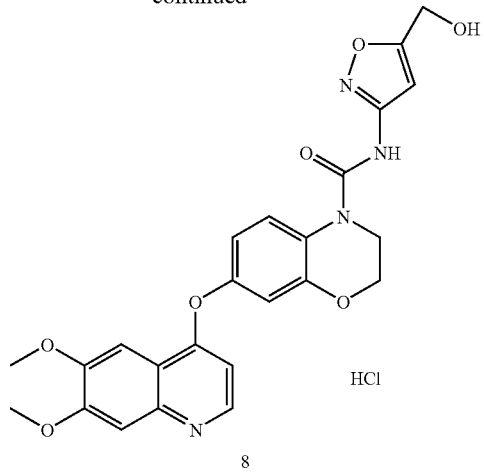

N-(5-((tert-butyldimethylsilyloxy)methyl)isoxazol-3-yl)-7-(6,7-dimethoxyquinolin-4-yloxy)-2,3-dihydrobenzo[b][1,4]oxazine-4-carboxamide (7)

To a resealable tube was added azido(5-((tert-butyldimethylsilyloxy)methyl)isoxazol-3-yl)methanone (5) (50 mg, 0.18 mmol), 7-(6,7-dimethoxyquinolin-4-yloxy)-3,4-dihydro-2H-benzo[b][1,4]oxazine (6) (20 mg, 0.059 mmol) and THF (1 mL). The tube was sealed and heated to 80° C. for 4 hrs. The solvent was removed in vacuo and the residue was purified by silica gel chromatography using 50-100% Hexanes:EtOAc to afford N-(5-((tert-butyldimethylsilyloxy)methyl)isoxazol-3-yl)-7-(6,7-dimethoxyquinolin-4-yloxy)-2,3-dihydrobenzo[b][1,4]oxazine-4-carboxamide (27 mg, 75% yield) as a white solid. MH+=593.2.

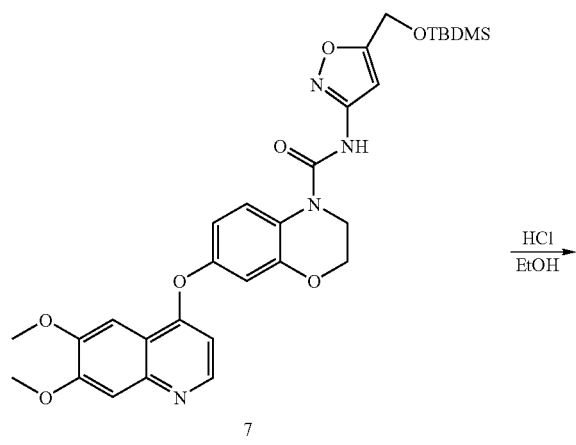

7-(6,7-dimethoxyquinolin-4-yloxy)-N-(5-(hydroxymethyl)isoxazol-3-yl)-2,3-dihydrobenzo[b][1,4]oxazine-4-carboxamide hydrochloride (8)

To N-(5-((tert-butyldimethylsilyloxy)methyl)isoxazol-3-yl)-7-(6,7-dimethoxyquinolin-4-yloxy)-2,3-dihydrobenzo[b][1,4]oxazine-4-carboxamide (7) (50 mg, 0.084 mmol) was added 2 N HCl in EtOH (5 mL) at RT. After 15 min, the solid had dissolved and the solution was stirred at RT for an additional 2 hrs at which time a white precipitate formed. The mixture was cooled to 0° C., filtered, and the isolated solid was washed with cold EtOH. The solid was dried in vacuo to afford 7-(6,7-dimethoxyquinolin-4-yloxy)-N-(5-(hydroxymethyl)isoxazol-3-yl)-2,3-dihydrobenzo[b][1,4]oxazine-4-carboxamide hydrochloride (33 mg, 83% yield). MH+=479.2.

Formulations

Also embraced within this invention is a class of pharmaceutical compositions comprising the active compounds of the current invention in association with one or more non-toxic, pharmaceutically-acceptable carriers and/or diluents and/or adjuvants (collectively referred to herein as "carrier" materials) and, if desired, other active ingredients. The active compounds of the present invention may be administered by any suitable route, preferably in the form of a pharmaceutical composition adapted to such a route, and in a dose effective for the treatment intended. The compounds and compositions of the present invention may, for example, be administered orally, mucosally, topically, rectally, pulmonarily such as by inhalation spray, or parentally including intravascularly, intravenously, intraperitoneally, subcutaneously, intramuscularly intrasternally and infusion techniques, in dosage unit formulations containing conventional pharmaceutically acceptable carriers, adjuvants, and vehicles.

The pharmaceutically active compounds of this invention can be processed in accordance with conventional methods of pharmacy to produce medicinal agents for administration to patients, including humans and other mammals.

For oral administration, the pharmaceutical composition may be in the form of, for example, a tablet, capsule, suspension or liquid. The pharmaceutical composition is preferably made in the form of a dosage unit containing a particular amount of the active ingredient. Examples of such dosage units are tablets or capsules. For example, these may contain an amount of active ingredient from about 50 micrograms to 2000 mg, preferably from about 1 to 500 mg. A suitable daily dose for a human or other mammal may vary widely depending on the condition of the patient and other factors, but, once again, can be determined using routine methods.

The amount of compounds which are administered and the dosage regimen for treating a disease condition with the compounds and/or compositions of this invention depends on a variety of factors, including the age, weight, sex and medical condition of the subject, the type of disease, the severity of the disease, the route and frequency of administration, and the particular compound employed. Thus, the dosage regimen may vary widely, but can be determined routinely using standard methods. A daily dose of about 0.001 to 500 mg/kg, preferably between about 0.01 and about 50 mg/kg, and more preferably about 0.001 and about 30 mg/kg body weight may be appropriate. The daily dose can be administered in one to four doses per day.

For therapeutic purposes, the active compounds of this invention are ordinarily combined with one or more adjuvants appropriate to the indicated route of administration. If administered per os, the compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets may contain a controlled-release formulation as may be provided in a dispersion of active compound in hydroxypropylmethyl cellulose.

In the case of psoriasis and other skin conditions, it may be preferable to apply a topical preparation of compounds of this invention to the affected area two to four times a day.

Formulations suitable for topical administration include liquid or semi-liquid preparations suitable for penetration through the skin (e.g., liniments, lotions, ointments, creams, or pastes) and drops suitable for administration to the eye, ear, or nose. A suitable topical dose of active ingredient of a compound of the invention is 0.1 mg to 150 mg administered one to four, preferably one or two times daily. For topical administration, the active ingredient may comprise from 0.001% to 10% w/w, e.g., from 1% to 2% by weight of the formulation, although it may comprise as much as 10% w/w, but preferably not more than 5% w/w, and more preferably from 0.1% to 1% of the formulation.

When formulated in an ointment, the active ingredients may be employed with either paraffinic or a water-miscible ointment base. Alternatively, the active ingredients may be formulated in a cream with an oil-in-water cream base. If desired, the aqueous phase of the cream base may include, for example at least 30% w/w of a polyhydric alcohol such as propylene glycol, butane-1,3-diol, mannitol, sorbitol, glycerol, polyethylene glycol and mixtures thereof. The topical formulation may desirably include a compound, which enhances absorption or penetration of the active ingredient through the skin or other affected areas. Examples of such dermal penetration enhancers include DMSO and related analogs.

The compounds of this invention can also be administered by a transdermal device. Preferably transdermal administration will be accomplished using a patch either of the reservoir and porous membrane type or of a solid matrix variety. In either case, the active agent is delivered continuously from the reservoir or microcapsules through a membrane into the active agent permeable adhesive, which is in contact with the skin or mucosa of the recipient. If the active agent is absorbed through the skin, a controlled and predetermined flow of the active agent is administered to the recipient. In the case of microcapsules, the encapsulating agent may also function as the membrane.

The oily phase of the emulsions of this invention may be constituted from known ingredients in a known manner. While the phase may comprise merely an emulsifier, it may comprise a mixture of at least one emulsifier with a fat or an oil or with both a fat and an oil. Preferably, a hydrophilic emulsifier is included together with a lipophilic emulsifier, which acts as a stabilizer. It is also preferred to include both an oil and a fat. Together, the emulsifier(s) with or without stabilizer(s) make-up the so-called emulsifying wax, and the wax together with the oil and fat make up the so-called emulsifying ointment base, which forms the oily dispersed phase of the cream formulations. Emulsifiers and emulsion stabilizers suitable for use in the formulation of the present invention include Tween 60, Span 80, cetostearyl alcohol, myristyl alcohol, glyceryl monostearate, sodium lauryl sulfate, glyceryl distearate alone or with a wax, or other materials well known in the art.

The choice of suitable oils or fats for the formulation is based on achieving the desired cosmetic properties, since the solubility of the active compound in most oils likely to be used in pharmaceutical emulsion formulations is very low. Thus, the cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters may be used. These may be used alone or in combination depending on the properties required. Alternatively, high melting point lipids such as white soft paraffin and/or liquid paraffin or other mineral oils can be used.

Formulations suitable for topical administration to the eye also include eye drops wherein the active ingredients are dissolved or suspended in suitable carrier, especially an aqueous solvent for the active ingredients. The active ingredients are preferably present in such formulations in a concentration of 0.5 to 20%, advantageously 0.5 to 10% and particularly about 1.5% w/w.

Formulations for parenteral administration may be in the form of aqueous or non-aqueous isotonic sterile injection solutions or suspensions. These solutions and suspensions may be prepared from sterile powders or granules using one or more of the carriers or diluents mentioned for use in the formulations for oral administration or by using other suitable dispersing or wetting agents and suspending agents. The compounds may be dissolved in water, polyethylene glycol, propylene glycol, ethanol, corn oil, cottonseed oil, peanut oil, sesame oil, benzyl alcohol, sodium chloride, tragacanth gum, and/or various buffers. Other adjuvants and modes of administration are well and widely known in the pharmaceutical art. The active ingredient may also be administered by injection as a composition with suitable carriers including saline, dextrose, or water, or with cyclodextrin (ie. Captisol), cosolvent solubilization (ie. propylene glycol) or micellar solubilization (ie. Tween 80).

The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed, including synthetic mono- or diglycerides. In addition, fatty acids such as oleic acid find use in the preparation of injectables.

For pulmonary administration, the pharmaceutical composition may be administered in the form of an aerosol or with an inhaler including dry powder aerosol.

Suppositories for rectal administration of the drug can be prepared by mixing the drug with a suitable non-irritating excipient such as cocoa butter and polyethylene glycols that are solid at ordinary temperatures but liquid at the rectal temperature and will therefore melt in the rectum and release the drug.

The pharmaceutical compositions may be subjected to conventional pharmaceutical operations such as sterilization and/or may contain conventional adjuvants, such as preservatives, stabilizers, wetting agents, emulsifiers, buffers etc. Tablets and pills can additionally be prepared with enteric coatings. Such compositions may also comprise adjuvants, such as wetting, sweetening, flavoring, and perfuming agents.

The foregoing is merely illustrative of the invention and is not intended to limit the invention to the disclosed compounds. Variations and changes, which are obvious to one skilled in the art are intended to be within the scope and nature of the invention, which are defined, in the appended claims.

From the foregoing description, one skilled in the art can easily ascertain the essential characteristics of this invention, and without departing from the spirit and scope thereof, can make various changes and modifications of the invention to adapt it to various usages and conditions.

No unacceptable toxological effects are expected when compounds of the present invention are administered in accordance with the present invention.

All mentioned references, patents, applications and publications, are hereby incorporated by reference in their entirety, as if here written.

We claim:
1. A compound selected from

A

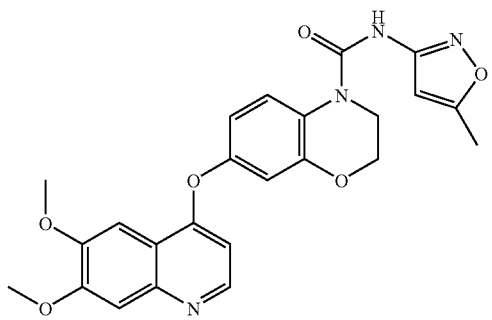

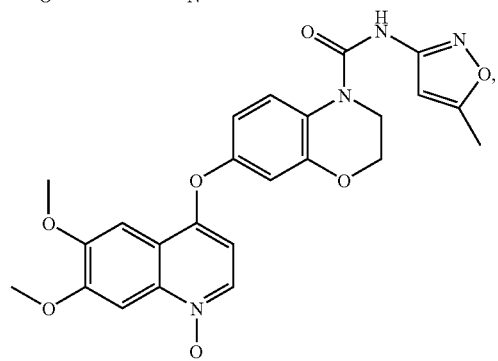

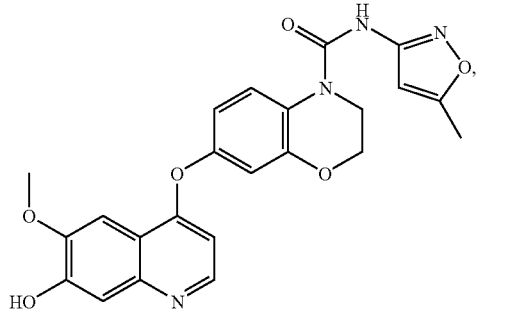

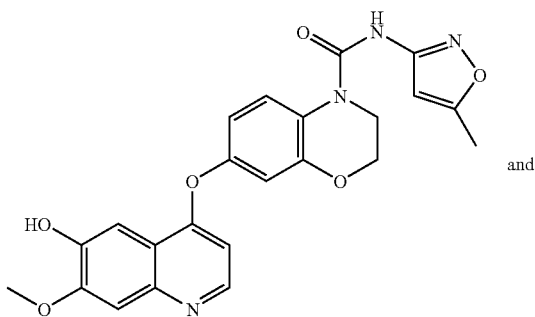

and

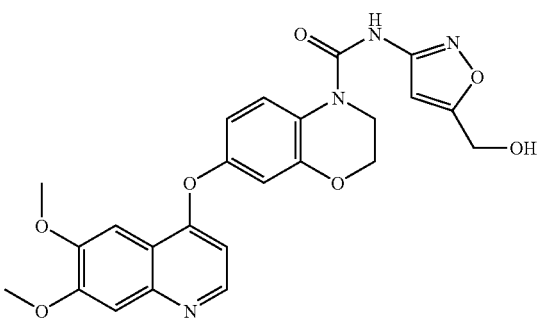

and pharmaceutically acceptable salts thereof.

2. A compound of claim 1 wherein said compound is the hydrochloride salt of compound A.

3. A compound of claim 1 wherein said compound is selected from

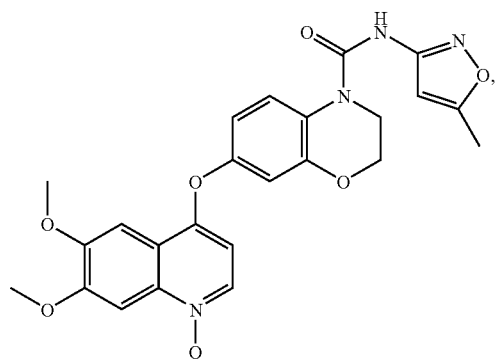

-continued

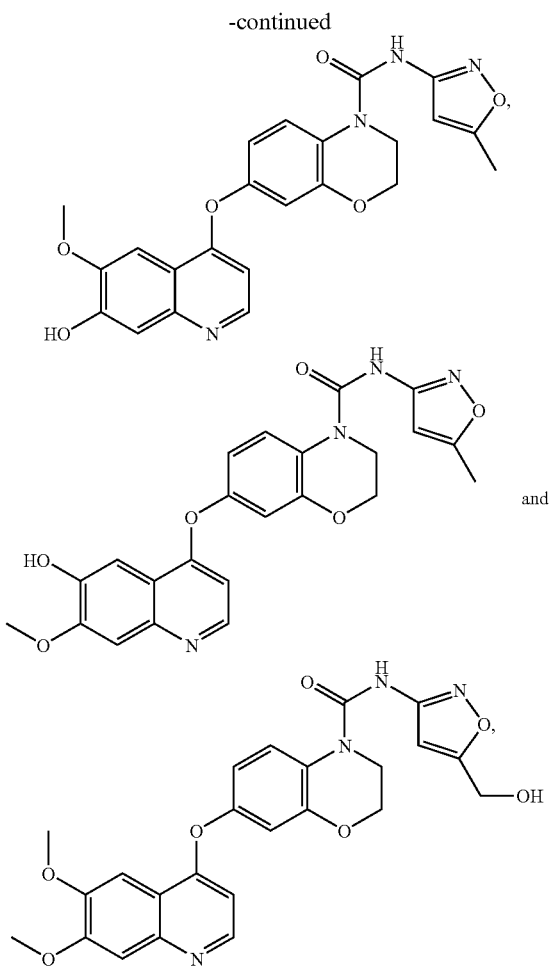

and pharmaceutically acceptable salts thereof.

4. A pharmaceutical composition comprising a compound of claim 1 or a pharmaceutically acceptable salt thereof, together with a pharmaceutically acceptable vehicle adjuvant or diluent.

5. A method of treating angiogenesis in a patient comprising administering to a patient in need of such treatment an effective amount of a compound of claim 1 or a pharmaceutically acceptable salt thereof.

6. A method of claim 5 wherein tumor growth is inhibited.

7. A process for preparing compound A

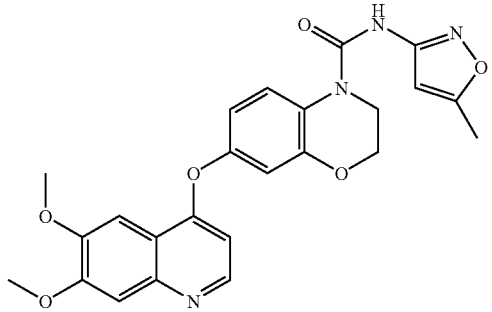

and pharmaceutically acceptable salts thereof comprising the step of contacting a compound of the following formula I

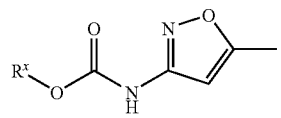

with a compound of the following formula II

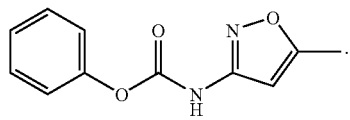

wherein R$^x$ is optionally substituted aryl or heteroaryl; in the presence of
(1) a polar solvent; and
(2) a base.

8. A process of claim 7 wherein the polar solvent comprises ethylacetate.

9. A process of claim 8 wherein the polar solvent is a mixture of ethylacetate and up to 20% by volume N-methyl pyrrolidinone.

10. A process of claim 7 wherein the base is potassium t-butoxide.

11. A process of claim 7 wherein the compound of formula II is

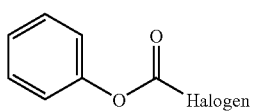

12. A process of claim 11 wherein the compound of formula II is prepared by contacting with a compound of the following formula III in the presence of
(1) a polar solvent; and
(2) a base.

13. A process of claim 12 wherein the compound of formula III is

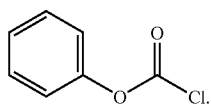

14. A process of claim 12 wherein the polar solvent is ethyl acetate.

15. A process of claim 12 wherein the base is potassium carbonate.

16. A process of claim 7 wherein the compound of formula I is prepared by contacting a compound of formula IV

IV

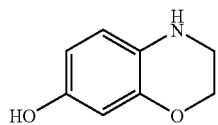

with a compound of formula V

V

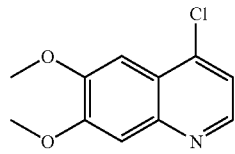

in the presence of N-methyl pyrrolidinone and potassium t-butoxide.

17. A process of claim 16 wherein the compound of formula IV is prepared by contacting a compound of formula VI

VI

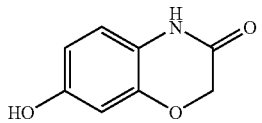

with $BH_3$, MeOH and HCl.

18. A process of claim 17 wherein the compound of formula VI is prepared by contacting a compound of formula VII

VII

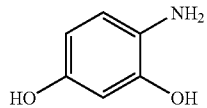

with a compound of formula VIII

VIII

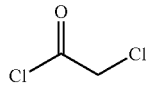

in the presence of potassium carbonate and toluene.

19. A compound made by the process of claim 7.

20. A compound of claim 1 and pharmaceutically acceptable salts thereof wherein said compound is 7-((6,7-bis(methyloxy)-4-quinolinyl)oxy)-N-(5-methyl-3-isoxazolyl)-2,3-dihydro-4H- 1,4-benzoxazine-4-carboxamide.

* * * * *